US009750761B2

(12) United States Patent
Kottmann et al.

(10) Patent No.: US 9,750,761 B2
(45) Date of Patent: Sep. 5, 2017

(54) LDH INHIBITORS AS TREATMENT FOR FIBROSIS AND FIBROTIC-RELATED DISORDERS

(71) Applicants: Robert M. Kottmann, Rochester, NY (US); Patricia J. Sime, Pittsford, NY (US); Richard P. Phipps, Pittsford, NY (US)

(72) Inventors: Robert M. Kottmann, Rochester, NY (US); Patricia J. Sime, Pittsford, NY (US); Richard P. Phipps, Pittsford, NY (US)

(73) Assignee: University of Rochester, Rochester, NY (US)

(*) Notice: Subject to any disclaimer, the term of this patent is extended or adjusted under 35 U.S.C. 154(b) by 0 days.

(21) Appl. No.: 14/718,933

(22) Filed: May 21, 2015

(65) Prior Publication Data

US 2015/0335674 A1  Nov. 26, 2015

Related U.S. Application Data

(60) Provisional application No. 62/001,325, filed on May 21, 2014.

(51) Int. Cl.
| | | |
|---|---|---|
| *A01N 35/00* | (2006.01) |
| *A61K 31/11* | (2006.01) |
| *A61K 31/713* | (2006.01) |
| *A61K 31/404* | (2006.01) |
| *A61K 45/06* | (2006.01) |
| *A61K 31/12* | (2006.01) |
| *C12N 15/113* | (2010.01) |

(52) U.S. Cl.
CPC ........... *A61K 31/713* (2013.01); *A61K 31/12* (2013.01); *A61K 31/404* (2013.01); *A61K 45/06* (2013.01); *C12N 15/1137* (2013.01); *C12Y 101/01027* (2013.01); *C12Y 101/01028* (2013.01); *C12N 2310/14* (2013.01); *C12N 2320/31* (2013.01)

(58) Field of Classification Search
None
See application file for complete search history.

(56) References Cited

U.S. PATENT DOCUMENTS

| 6,608,107 B2 * | 8/2003 | Wong ................... A61K 31/22 |
| | | 514/548 |
| 2011/0091552 A1 | 4/2011 | McCaffrey et al. |
| 2012/0309794 A1 | 12/2012 | Minutolo et al. |
| 2013/0150440 A1 | 6/2013 | Nagai et al. |

OTHER PUBLICATIONS

Benz et al. J. Clin. Invest. (1987), vol. 79, pp. 517-523.*
Atzori et al. Thorax (2004), vol. 59, pp. 217-223.*
Prud'homme Laboratory Investigation (2007), vol. 87, pp. 1077-1091.*
Ziesche et al. The New England Journal of Medicine (1999), vol. 341, pp. 1264-1269.*
Kulkarni, Ajit A., et al. "The Lactate Dehydrogenase Inhibitor Gossypol Inhibits Bleomycin Induced Pulmonary Fibrosis." D41. The Bleomycin Model of Lung Fibrosis and Beyond. American Thoracic Society, 2013. A5656-A5656.*
Kuwano et al. Current Molecular Medicine (2001), vol. 1, pp. 551-573.*
Kottmann et al., "The Lactate Dehydrogenase Inhibitor Gossypol Inhibits Bleomycin Induced Pulmonary Fibrosis," Am. J. Respir. Crit. Care Med. 187:A5656 (May 22, 2013).
Kottmann et al., "Lactic Acid is Elevated in Idiopathic Pulmonary Fibrosis and Induces Myofibroblast Differentiation via pH Dependent Activation of Transforming Growth Factor-Beta," Am. J. Respir. Crit. Care Med. 186(8):740-751 (2012).

* cited by examiner

*Primary Examiner* — Patrick Lewis
(74) *Attorney, Agent, or Firm* — LeClairRyan, a Professional Corporation

(57) ABSTRACT

One aspect of the disclosure relates to methods of treating a fibrotic condition in an individual. The methods include administering to an individual having a fibrotic condition an effective amount of a lactic dehydrogenase (LDH) inhibitor, wherein the fibrotic condition involves an internal organ or tissue, or ocular tissue, and said administering is effective to treat the fibrotic condition. Methods of administration and pharmaceutical compositions and systems for practicing such methods are also disclosed.

15 Claims, 15 Drawing Sheets

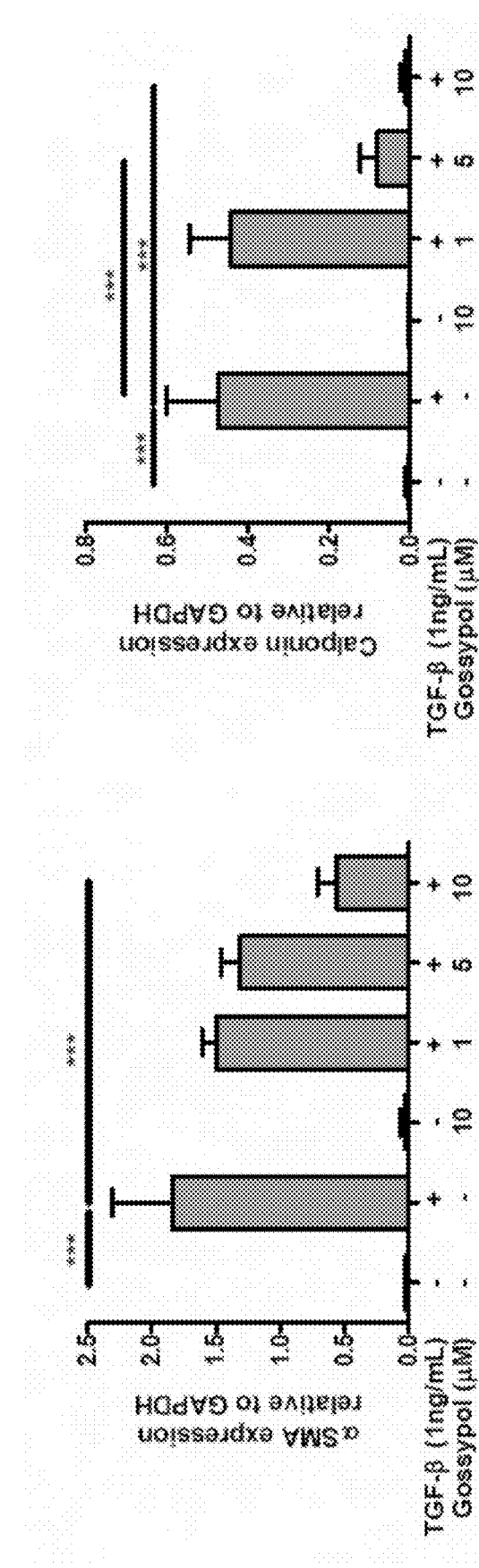
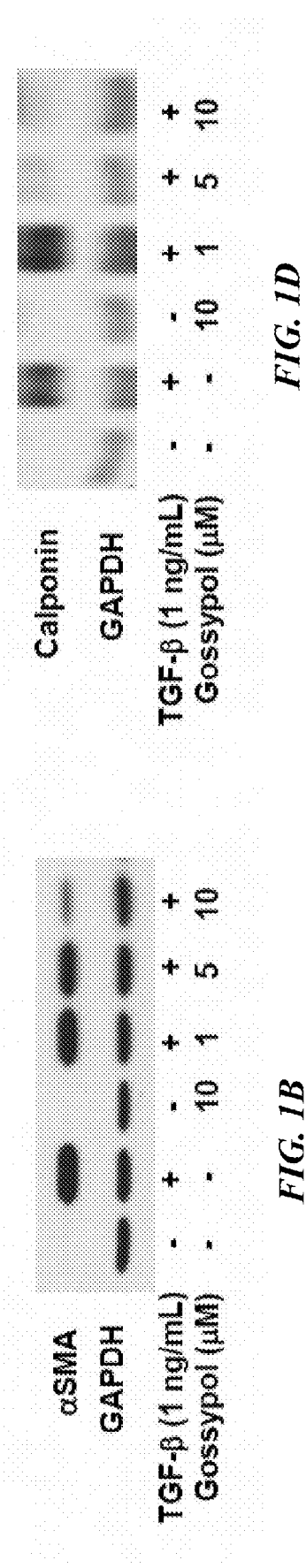
FIG. 1A
FIG. 1B
FIG. 1C
FIG. 1D

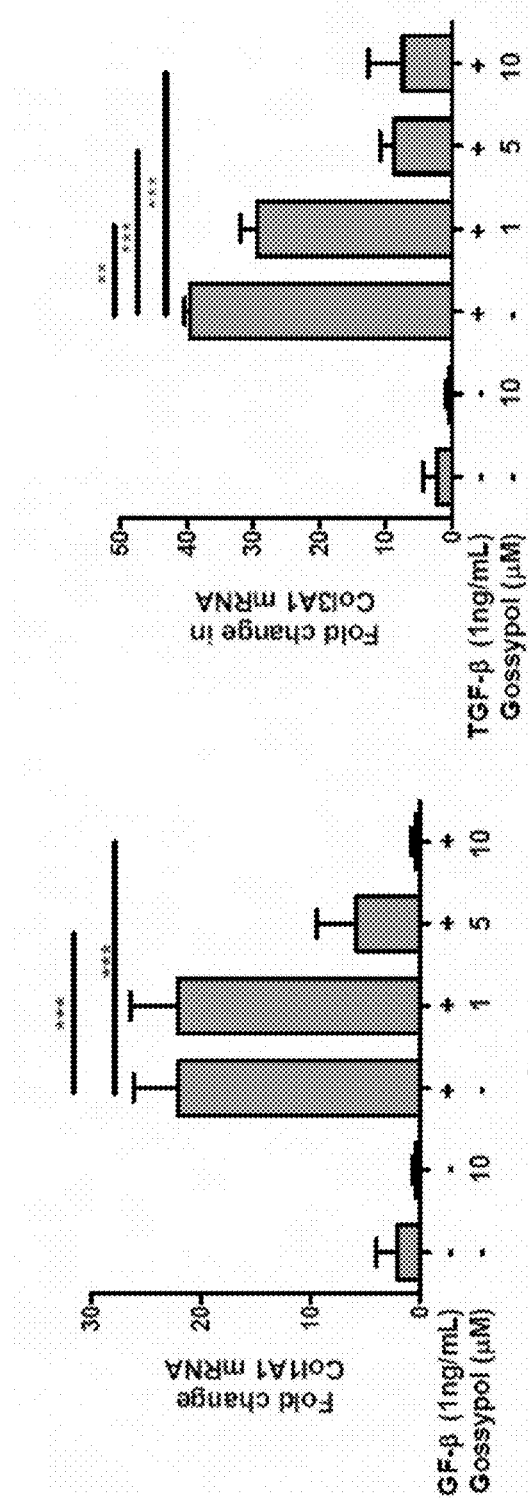
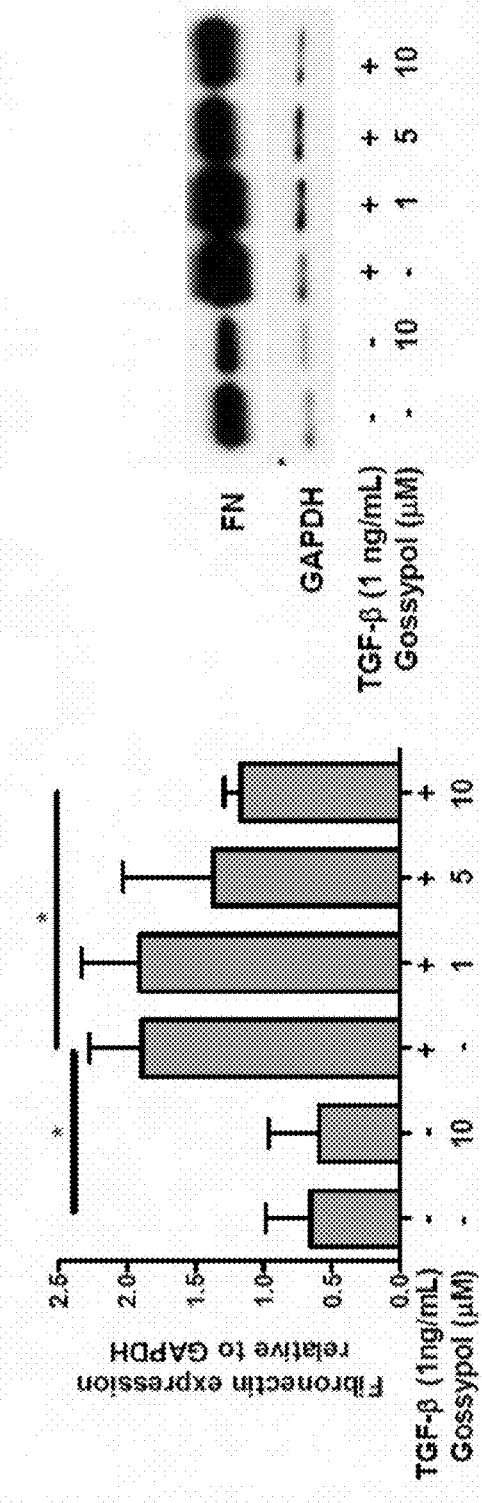
FIG. 3A  FIG. 3B  FIG. 3C  FIG. 3D

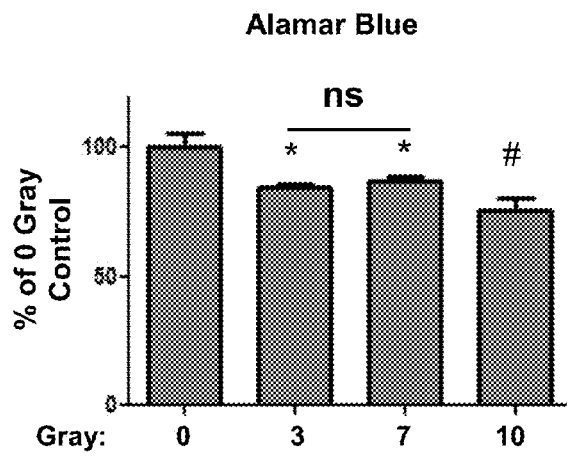
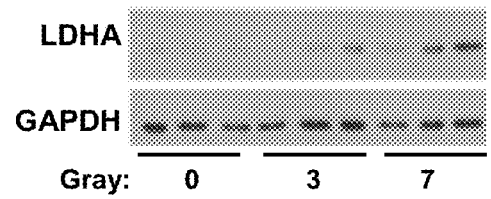
FIG. 11A
FIG. 11B
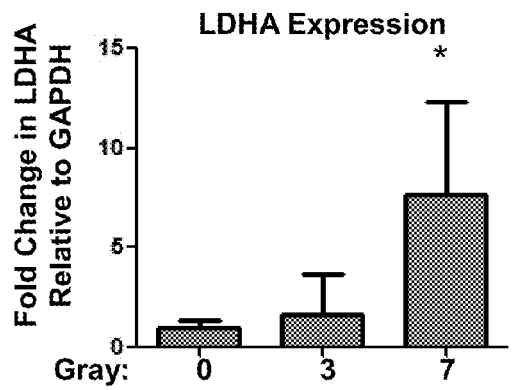
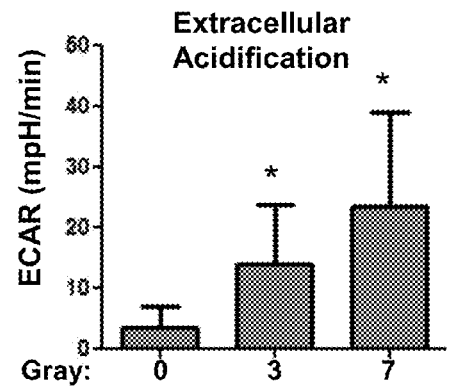
FIG. 11C
FIG. 11D
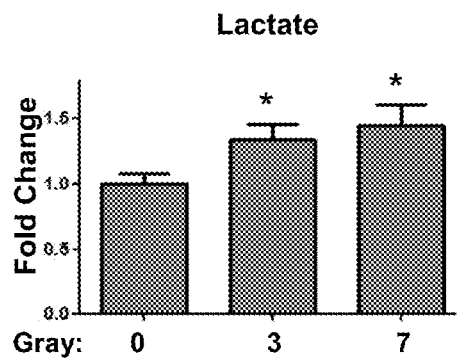
FIG. 11E

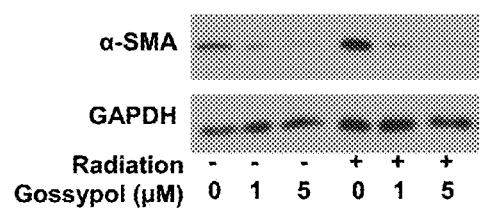
FIG. 15A
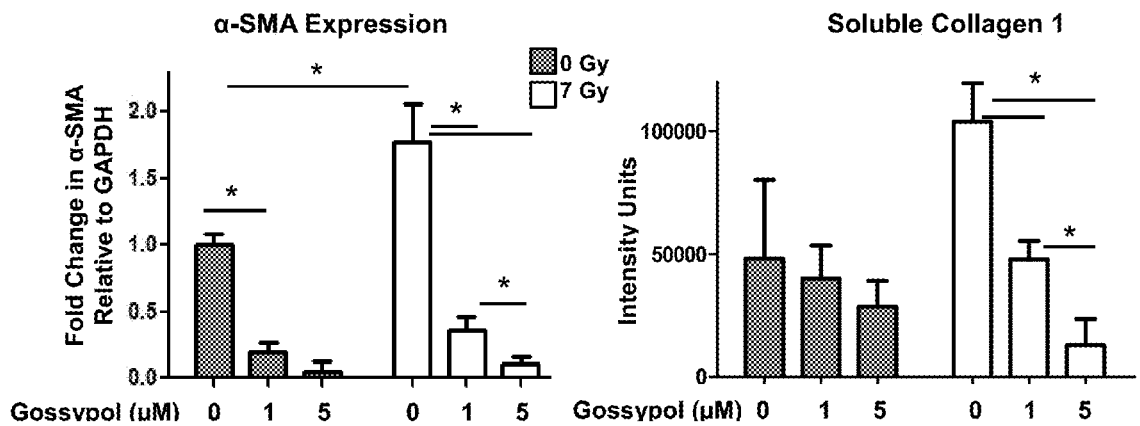
FIG. 15B  FIG. 15C

LDH INHIBITORS AS TREATMENT FOR FIBROSIS AND FIBROTIC-RELATED DISORDERS

This application claims the priority benefit of U.S. Provisional Patent Application Ser. No. 62/001,325 filed May 21, 2014, which is hereby incorporated by reference in its entirety.

This invention was made with government support under RR024160; HL075432; HL066988; ES001247; RR024136 awarded by the National Institutes of Health. The government has certain rights in the invention.

FIELD OF THE TECHNOLOGY

The technology disclosed herein is directed to methods of treating and preventing fibrosis and fibrotic-related disorders in an individual, as well as pharmaceutical compositions and system useful for such methods.

BACKGROUND

Normal tissue repair processes are critical for maintaining proper tissue function. Tissue fibrosis is characterized by the abnormal accumulation of extracellular matrix ("ECM") that is thought to arise from unresolved tissue repair (Selman et al., "Idiopathic Pulmonary Fibrosis: Prevailing and Evolving Hypotheses About its Pathogenesis and Implications for Therapy," Ann. Intern. Med. 134(2):136-151 (2001); Mutsaers et al., "Mechanisms of Tissue Repair: From Wound Healing to Fibrosis," Int. J. Biochem. Cell Biol. 29(1):5-17 (1997)). Fibrosis affects many organ systems including, among others, the lung, kidney, liver and heart; and many disease processes, including cardiomyopathies, hypertension, chronic hepatitis C infection, adult respiratory distress syndrome, and sarcoidosis are accompanied by fibrosis (Pugin et al., "The Alveolar Space is the Site of Intense Inflammatory and Profibrotic Reactions in the Early Phase of Acute Respiratory Distress Syndrome," Crit. Care Med. 27(2):304-312 (1999); Bedossa et al., "Liver Extracellular Matrix in Health and Disease," J. Pathol. 200(4):504-515 (2003); Heling et al., "Increased Expression of Cytoskeletal, Linkage, and Extracellular Proteins in Failing Human Myocardium," Circ. Res. 86(8):846-853 (2000); Intengan et al., "Vascular Remodeling in Hypertension: Roles of Apoptosis, Inflammation, and Fibrosis," Hypertension. 38(3 Pt 2):581-587 (2001); and Berk et al., "ECM Remodeling in Hypertensive Heart Disease," J. Clin. Invest. 117(3):568-575 (2007)).

Tissue repair is a multi-step process that is initiated upon tissue injury and involves platelet activation, blood clotting, and the local release of inflammatory mediators and cytokines Following injury, fibronectin is crosslinked into the fibrin clot (Hynes R., Fibronectins (Springer-Verlag 1990); Colvin R., "Fibronectin in Wound Healing," In Fibronectin (Mosher D. ed., 1989)), where it promotes the migration and attachment of fibroblasts, endothelial cells, monocytes and neutrophils (Hynes R., Fibronectins (Springer-Verlag 1990); Colvin R., "Fibronectin in Wound Healing," In Fibronectin (Mosher D. ed., 1989); and Grinnell et al., "Fibroblast Adhesion to Fibrinogen and Fibrin Substrata: Requirement for Cold-Insoluble Globulin (Plasma Fibronectin)," Cell 19:517-525 (1980)). In later stages of tissue repair, the fibronectin-rich provisional matrix is replaced by granulation tissue, which is rich in collagen. Fibronectin matrix polymerization is required for deposition of collagen I fibrils (Sottile et al., "Fibronectin Polymerization Regulates the Composition and Stability of Extracellular Matrix Fibrils and Cell-Matrix Adhesions," Mol. Biol. Cell. 13:3546-3559 (2002); Sottile et al., "Fibronectin-Dependent Collagen I Deposition Modulates the Cell Response to Fibronectin," Am. J. Physiol. Cell Physiol. 293:C1934-1946 (2007); Velling et al., "Polymerization of Type I and III Collagens is Dependent on Fibronectin and Enhanced by Integrins alpha 11-beta 1 and alpha 2-beta 1," J. Biol. Chem. 277(40): 37377-37381 (2002); and McDonald et al., "Role of Fibronectin in Collagen Deposition: Fab' to the Gelatin-Binding Domain of Fibronectin Inhibits both Fibronectin and Collagen Organization in Fibroblast Extracellular Matrix," J. Cell. Biol. 92:485-492 (1982)).

Contraction of myofibroblasts within the granulation tissue serves to reduce the area of the wound and to enhance the mechanical strength of regenerating tissue (Mutsaers et al., "Mechanisms of Tissue Repair: From Wound Healing to Fibrosis," Int. J. Biochem. Cell Biol. 29(1):5-17 (1997)). Fibronectin matrix polymerization is an important regulator of cell growth, cell migration, cell contractility, and ECM remodeling (Sottile et al., "Fibronectin Polymerization Regulates the Composition and Stability of Extracellular Matrix Fibrils and Cell-Matrix Adhesions," Mol. Biol. Cell. 13:3546-3559 (2002); Sottile et al., "Fibronectin-Dependent Collagen I Deposition Modulates the Cell Response to Fibronectin," Am. J. Physiol. Cell Physiol. 293:C1934-1946 (2007); Hocking et al., "Stimulation of Integrin-Mediated Cell Contractility by Fibronectin Polymerization," J. Biol. Chem. 275:10673-10682 (2000); Sottile et al., "Fibronectin Matrix Assembly Enhances Adhesion-Dependent Cell Growth," J. Cell Sci. 111:2933-2943 (1998)), and as such, is an important regulator of tissue repair.

Many of the processes that occur in normal tissue repair also occur during fibrosis (Selman et al., "Idiopathic Pulmonary Fibrosis: Prevailing and Evolving Hypotheses About its Pathogenesis and Implications for Therapy," Ann. Intern. Med. 134(2):136-151 (2001) and Mutsaers et al., "Mechanisms of Tissue Repair: From Wound Healing to Fibrosis," Int. J. Biochem. Cell Biol. 29(1):5-17 (1997)). In fibrotic disorders, abnormal, excessive deposition of ECM leads to a disruption of normal tissue architecture and impaired organ function (Selman et al., "Idiopathic Pulmonary Fibrosis: Prevailing and Evolving Hypotheses About its Pathogenesis and Implications for Therapy," Ann. Intern. Med. 134(2):136-151 (2001); Zeisberg et al., "Role of Fibroblast Activation in Inducing Interstitial Fibrosis," J. Nephrol. 13 Suppl 3:S111-120 (2000); Fang, K C., "Mesenchymal Regulation of Alveolar Repair in Pulmonary Fibrosis," Am. J. Respir. Cell Mol. Biol. 23(2):142-145 (2000)). Enhanced fibronectin and collagen deposition is associated with fibrotic diseases including interstitial pulmonary fibrosis (Selman et al., "Idiopathic Pulmonary Fibrosis: Prevailing and Evolving Hypotheses About its Pathogenesis and Implications for Therapy," Ann. Intern. Med. 134(2):136-151 (2001); McDonald J., "Fibronectin In the Lung," In Fibronectin (Mosher D. ed., 1989)); Demling R H., "The Modern Version of Adult Respiratory Distress Syndrome," Ann. Rev. Med. 46:193-202 (1995); Gauldie et al., "TGF-β, Smad3 and the Process of Progressive Fibrosis," Biochem. Soc. Trans. 35(Pt 4):661-664 (2007)), renal fibrosis (Zeisberg et al., "Role of Fibroblast Activation in Inducing Interstitial Fibrosis," J. Nephrol. 13 Suppl 3:S111-120 (2000)), liver fibrosis (Brenner, D. A., "Molecular Pathogenesis of Liver Fibrosis," Trans. Am. Clin. Climatol. Assoc. 120:361-368 (2009); Friedman, S. L., "Hepatic Stellate Cells: Protean, Multifunctional, and Enigmatic Cells of the Liver," Physiol. Rev. 88:125-172 (2008); Bedossa et al., "Liver Extracellular Matrix in Health and Disease," *J. Pathol* 200:504-515 (2003)), and cardiac fibrosis (Heling et al., "Increased Expression of Cytoskeletal, Linkage, and Extracellular Proteins in Failing Human Myocardium," *Circ. Res.* 86(8):846-853 (2000); van Dijk et al., "Accumulation of Fibronectin in the Heart after Myocardial Infarction: A Putative Stimulator of Adhesion and Proliferation of Adipose-Derived Stem Cells," *Cell Tissue Res.* 332(2):289-298 (2008); Tsutsumi et al., "Angiotensin II Type 2 Receptor is Upregulated in Human Heart with Interstitial Fibrosis, and Cardiac Fibroblasts are the Major Cell Type for its Expression," *Circ. Res.* 83(10):1035-1046 (1998)). Persistent fibroblast "activation" is thought to lead to continued fibroblast proliferation, excessive ECM production, and aberrant ECM remodeling. The underlying cause of this fibroblast "activation" is unknown, but may result from chronic inflammation, abnormal fibroblast response to growth factors, altered cell response to ECM, an altered balance of matrix degradation and deposition, and/or aberrant interactions between epithelial and mesenchymal cells (Selman et al., "Idiopathic Pulmonary Fibrosis: Prevailing and Evolving Hypotheses About its Pathogenesis and Implications for Therapy," *Ann. Intern. Med.* 134(2):136-151 (2001); Butler et al., "Current Progress in Keloid Research and Treatment," *J. Am. Coll. Surg.* 206(4):731-741 (2008); Zeisberg et al., "Role of Fibroblast Activation in Inducing Interstitial Fibrosis," *J. Nephrol.* 13 Suppl 3:S111-120 (2000); Gauldie et al., "TGF-β, Smad3 and the Process of Progressive Fibrosis," *Biochem. Soc. Trans.* 35(Pt 4):661-664 (2007); Eckes et al., "Fibroblast-Matrix Interactions in Wound Healing and Fibrosis," *Matrix Biol.* 19(4):325-332 (2000)).

Despite these insights into the fibrotic processes associated with fibrotic disease development, there remains a need for pharmacological agents that can effectively control the development and progression of fibrotic disease. The disclosed technology is directed to overcoming these and other deficiencies in the art.

SUMMARY

A first aspect relates to a method of treating a fibrotic condition in an individual. This method includes administering to an individual having a fibrotic condition an effective amount of a lactic dehydrogenase ("LDH") inhibitor, wherein the fibrotic condition involves an internal organ or tissue, or ocular tissue, and said administering is effective to treat the fibrotic condition.

A second aspect relates to a method of treating a fibrotic condition in an individual. This method consists essentially of administering to an individual having a fibrotic condition an effective amount of an LDH inhibitor, wherein the fibrotic condition involves an internal organ or tissue, or ocular tissue, and said administering is effective to treat the fibrotic condition.

In certain embodiments of the first and second aspect, the fibrotic condition being treated excludes a cancerous proliferative disorder, idiopathic arthrofibrosis, and dermatological scarring.

A third aspect relates to a pharmaceutical composition or system that includes therapeutically effective amounts of an LDH inhibitor and at least one additional anti-fibrotic agent, each in a pharmaceutically acceptable carrier.

According to this aspect, the LDH inhibitor and the at least one additional anti-fibrotic agent can be present in the same pharmaceutically acceptable carrier, i.e., in the form of a single composition. Alternatively, LDH inhibitor and the at least one additional anti-fibrotic agent can be present in different compositions, which may or may not include the same pharmaceutically acceptable carrier.

Lactic acid concentrations and expression of LDH are increased in idiopathic pulmonary fibrosis ("IPF") and play an important role in the pathogenesis of the fibrotic condition (Kottmann et al., "Lactic Acid is Elevated in Idiopathic Pulmonary Fibrosis and Induces Myofibroblast Differentiation Via pH-Dependent Activation of Transforming Growth Factor-Beta," *Am. J. Respir. Crit. Care Med.* 186:740-751 (2012), which is hereby incorporated by reference in its entirety. By overexpressing LDH via plasmid transfection in fibroblasts, latent transforming growth factor beta ("TGF-β") is activated in a pH dependent manner and myofibroblast differentiation is induced. In addition, LDH inhibition by siRNA effectively blocks TGF-β-induced myofibroblast differentiation. Importantly, the accompanying Examples demonstrate that both genetic and pharmacologic inhibition of LDH inhibit TGF-β-induced myofibroblast differentiation in vitro. Myofibroblast differentiation is believed to be integral to the development of pulmonary fibrosis and other forms of fibrosis, and therefore pharmacologic inhibition of LDH using an LDH inhibitor will inhibit in vivo myofibroblast differentiation in various fibrotic conditions, including pulmonary fibrosis and other forms of fibrosis as disclosed herein. The Examples also demonstrate that LDHA is upregulated in radiation-induced fibrosis lung tissue and in irradiated lung fibroblasts, that lactate is required for radiation-induced myofibroblast differentiation, and that inhibition of LDHA activity prevents radiation-induced myofibroblast differentiation in primary human lung fibroblast cultures. These studies implicate LDHA as a therapeutic target for treating and preventing radiation-induced pulmonary fibrosis, and offer a rationale for treating or preventing other forms of radiation-induced fibrosis, including radiation-induced liver or skin fibrosis.

BRIEF DESCRIPTION OF THE DRAWINGS

FIGS. 1A-1E show that the LDH inhibitor gossypol inhibits TGF-β induced myofibroblast differentiation. Normal primary human lung fibroblasts were cultured with and without 1 ng/mL TGF-β and/or 1, 5, or 10 mM gossypol for 72 hours. Western blot ("WB") analysis of protein lysates were performed for markers of myofibroblast differentiation, αSMA (FIGS. 1A-1B) and calponin (FIGS. 1C-1D). Densitometry for n=3 replicates per condition, and representative WB images are shown. (Mean±SD (or SEM) shown, ***=p<0.001 by ANOVA compared to untreated cells); FIG. 1E shows immunofluorescence analysis for αSMA performed on cell cultures treated with and without TGF-β and/or 10 mM gossypol. Three strains of primary normal lung fibroblasts were tested, results from one representative strain are shown.

FIGS. 3A-3D show that gossypol inhibits TGF-β induced extracellular matrix generation. Primary human lung fibroblasts were cultured with and without 1 ng/mL TGF-β and/or 1, 5, or 10 mM gossypol for 24 hours. Col1A1 (FIG. 3A) and Col3A1 (FIG. 3B) mRNA induction was analyzed using qRT-PCR. (Mean±SD, *=$p<0.001$, =$p<0.01$ by ANOVA compared to untreated cells). FIGS. 3C-3D show WB analysis of protein lysates performed for fibronectin expression. Densitometry for n=3 replicates, and representative WB images are shown. (ANOVA * $p<0.05$)

Fibroblasts were transfected with either LDHA siRNA or a control siRNA and subsequently cultured with and without 1 ng/mL TGF-β and/or 5 mM gossypol for 72 hours. WB analysis of protein lysates were performed for αSMA expression. FIG. 5A shows densitometry for n=3 replicates per group (Mean±SD, ***=$p<0.001$, *=$p<0.05$ ANOVA compared to untreated cells). FIG. 5B shows representative WB of cells treated with gossypol and LDH or scrambled siRNA without TGF-β. FIG. 5C shows representative WB of cells treated with gossypol and LDH or scrambled siRNA plus 1 ng/ml TGF-β.

FIGS. 6A-6B=10× magnification; FIG. 6C-6E=40× magnification.

FIG. 7A shows that gossypol significantly reduced Col1A1 mRNA expression.

FIG. 7B shows that there was a trend toward a reduction in bleomycin-induced fibronectin mRNA expression in mice treated with gossypol.

FIGS. 10A-D illustrate lung biopsies that were obtained from patients who received thoracic radiation for cancer treatment and from non-irradiated controls, immunostained for α-SMA or LDHA, and developed with Nova Red. FIG. 10A illustrates non-fibrotic lung sections which were stained for LDHA. FIGS. 10B-10C show serial paraffin embedded tissue sections from radiation-induced fibrotic lung tissue which were stained for LDHA and α-SMA. FIG. 10D shows radiation-induced fibrotic lung tissue stained with Gomori Trichome. FIGS. 10E-10G illustrate results from C57BL/6 mice which were exposed to 5 Gy total body plus 10 Gy thoracic radiation, and were harvested at 12-26 weeks post-radiation. Paraffin embedded lung tissue sections from control (FIG. 10E) and irradiated (FIG. 10F) mice at 26 weeks post radiation were stained for LDHA. FIG. 10G is a graph illustrating RNA isolated from whole lung homogenates, where mRNA levels of LDHA were measured by quantitative real-time PCR and normalized to GAPDH. Isotype controls for immunohistochemical staining are inset in FIGS. 10B, 10E. Scale bars represent 100 μm. *$p \leq 0.05$ by ANOVA compared to non-irradiated control, n=3-8 mice per group.

FIGS. 11A-E illustrate that ionizing radiation induces LDHA expression, lactate production, and extracellular acidification in lung fibroblasts. Primary human lung fibroblasts were exposed to 0, 3, 7, and 10 Gy radiation from a $^{137}$Cs γ-ray source and cell lysates and supernatants were collected at 5 days post-radiation. FIG. 11A is a graph showing cell viability measured using an Alamar blue assay of mitochondrial activity (n=3). FIG. 11B shows LDHA protein expression analyzed by WB. One representative experiment is shown (n=3). FIG. 11C is a graph showing LDHA expression relative to GAPDH as determined by densitometry and normalized to 0 Gy control. FIG. 11D is a graph showing extracellular acidification rates ("ECAR") measured using a Seahorse Bioscience XF96 Flux Analyzer (n=10-12). FIG. 11E is a graph showing lactate levels measured in the supernatants using a Nova BioProfile Automated Analyzer (n=3). * p≤0.05 compared to 0 Gy control by ANOVA. #p≤0.05 compared to 3 and 7 Gy. ns=no statistical significance.

FIGS. 12A-12B illustrate α-SMA protein expression analyzed by WB and densitometry. One representative experiment is shown (*p≤0.05 by ANOVA compared to 0 Gy, n=3). FIG. 12C is a panel of images illustrating immunofluorescence staining for α-SMA (red) performed on cell cultures exposed to 7 Gy radiation or transforming growth factor-beta (TGF-β). Cell nuclei were stained with DAPI. FIG. 12D is a graph showing soluble collagen measured in supernatants from irradiated cells cultures at 5 days post radiation using a Slot Blot Assay (*p≤0.05 by ANOVA compared to 0 Gy, n=3). FIGS. 12E-12F are graphs showing total RNA isolated from cells exposed to 7 Gy radiation at 3 days post-radiation and quantitative real time PCR performed for Col1a1 and Col3a1 (*p≤0.05 by t-test, n=3).

FIG. 13A shows TGF-β bioactivity measured using a mink lung cell proliferation assay. Mink lung cells were incubated with supernatants from primary human lung fibroblast cell cultures exposed to 0 or 7 Gy radiation and proliferation was measured using 3H-thymidine incorporation. Inverse of proliferation rates relative to 0 Gy controls were plotted (*p≤0.05 by t-test, n=3). FIGS. 13B-13C show the effects of lung fibroblasts pretreated with a TGF-β receptor 1 inhibitor (SB431542) 1 hr prior to exposure to 0 or 7 Gy radiation. Cell lysates were collected 5 days post radiation and were analyzed for α-SMA protein expression levels by WB and densitometry (*p≤0.05 by ANOVA, n=3).

FIGS. 14A-14B show cell lysates collected 5 days post radiation and analyzed for LDHA and α-SMA protein expression levels by WB and densitometry. (n=3). FIG. 14C is a graph showing TGF-β bioactivity measured in cell supernatants using a mink lung cell bioassay (n=6). FIG. 14D is a graph showing ECAR measured using a Seahorse Bioscience XF96 Flux Analyzer (n=20-22). p≤0.05 by ANOVA.

FIGS. 15A-C show that gossypol, an LDH inhibitor, inhibits radiation-induced myofibroblast differentiation. FIGS. 15A-15B show primary human lung fibroblasts which were pretreated with gossypol at 1 and 5 μM starting 1 hr prior to irradiation with 0 or 7 Gy, and then cell lysates were collected 5 days post radiation and analyzed for α-SMA protein expression levels by WB and densitometry. One representative set of conditions is shown (n=3). FIG. 15C is a graph showing Soluble collagen 1 measured in culture supernatants using a Slot Blot Assay (n=3). *p≤0.05 by ANOVA.

DETAILED DESCRIPTION OF THE INVENTION

Figure 1E:
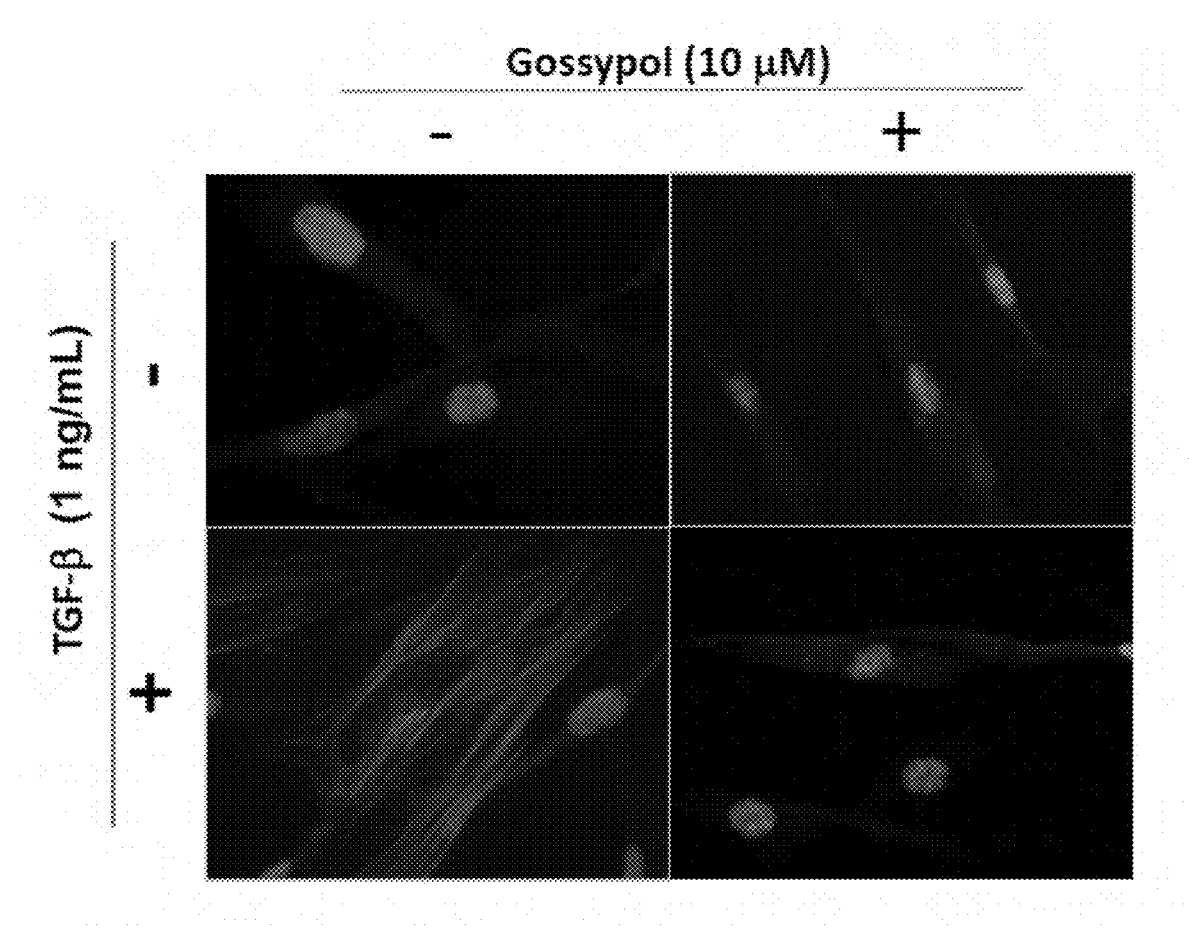

A first aspect relates to methods for the treatment of a fibrotic condition in an individual. This method includes administering to an individual having a fibrotic condition an effective amount of a lactic dehydrogenase inhibitor, wherein the fibrotic condition involves an internal organ or tissue, or ocular tissue, and the administration of the lactic dehydrogenase inhibitor is effective to treat the fibrotic condition.

A number of fibrotic conditions can be treated in accordance with the present invention, including those involving internal organs such as lung, liver, kidney, heart, pancreas, gastrointestinal organs, and genitourinary organs; vascular tissue; and ocular tissue such as corneal tissue or retinal tissue.

Exemplary fibrotic conditions of the lung (i.e., pulmonary fibrosis) include, but are not limited to, idiopathic pulmonary fibrosis ("IPF"); idiopathic pulmonary upper lobe fibrosis (Amitani disease); familial pulmonary fibrosis; pulmonary fibrosis secondary to systemic inflammatory diseases such as, rheumatoid arthritis, scleroderma, lupus, cryptogenic fibrosing alveolitis, chronic obstructive pulmonary disease ("COPD") or chronic asthma or secondary to radiation exposure; cystic fibrosis; non-specific interstitial pneumonia ("NSIP"); cryptogenic organizing pneumonia ("COP"); progressive massive fibrosis, a complication of coal worker's pneumoconiosis; scleroderma/systemic sclerosis; bronchiolitis obliterans-organizing pneumonia; pulmonary hypertension; pulmonary tuberculosis; silicosis; asbestosis; acute lung injury; and acute respiratory distress ("ARD"; including bacterial pneumonia induced, trauma-induced, and viral pneumonia-induced, ventilator-induced, non-pulmonary sepsis induced).

Exemplary fibrotic conditions of the liver (i.e., liver fibrosis) include, but are not limited to, liver cirrhosis due to all etiologies; congenital hepatic fibrosis; obesity; fatty liver; alcohol induced liver fibrosis; non-alcoholic steatohepatitis (NASH); biliary duct injury; primary biliary cirrhosis; infection- or viral-induced liver fibrosis (e.g., chronic hepatitis B and C virus infections); cystic fibrosis; autoimmune hepatitis; necrotizing hepatitis; primary sclerosing cholangitis; hemochromatosis; disorders of the biliary tree; hepatic dysfunction attributable to infections; and fibrosis secondary to radiation exposure.

Exemplary fibrotic conditions of the heart and/or pericardium (i.e., heart or pericardial fibrosis, or fibrosis of the associate vasculature) include, but are not limited to, endomyocardial fibrosis; cardiac allograft vasculopathy ("CAV"); myocardial infarction; atrial fibrosis; congestive heart failure; arterioclerosis; atherosclerosis; vascular stenosis; myocarditis; congestive cardiomyopathy; coronary infarcts; varicose veins; coronary artery stenosis and other post-ischemic conditions; and idiopathic retroperitoneal fibrosis.

Exemplary fibrotic conditions of the kidney (i.e., kidney fibrosis) include, but are not limited to, glomerulonephritis (including membranoproliferative, diffuse proliferative, rapidly progressive or sclerosing, post-infectious and chronic forms); diabetic glomerulosclerosis; focal segmental glomerulosclerosis; IgA nephropathy; diabetic nephropathy; HIV-associated nephropathy; membrane nephropathy;

glomerulonephritis secondary to systemic inflammatory diseases such as lupus, scleroderma and diabetes glomerulonephritis; idiopathic membranoproliferative glomerular nephritis; mesangial proliferative glomerulonephritis; crescentic glomerulonephritis; amyloidosis (which affects the kidney among other tissues); autoimmune nephritis; renal tubuloinsterstitial fibrosis; renal arteriosclerosis; Alport's syndrome; nephrotic syndrome; chronic renal failure; periglomerular fibrosis/atubular glomeruli; combined apical emphysema and basal fibrosis syndrome (emphysema/fibrosis syndrome); glomerular hypertension; nephrogenic fibrosing dermatopathy; polycystic kidney disease; Fabry's disease and renal hypertension.

Exemplary fibrotic conditions of the pancreas (i.e., pancreatic fibrosis) include, but are not limited to, stromal remodeling pancreatitis and stromal fibrosis.

Exemplary fibrotic conditions of the gastrointestinal tract (i.e., GI tract fibrosis) include, but are not limited to, Crohn's disease; ulcerative colitis; collagenous colitis; colorectal fibrosis; villous atrophy; crypt hyperplasia; polyp formation; healing gastric ulcer; and microscopic colitis.

Exemplary fibrotic conditions of the eye include, but are not limited to, ocular fibrosis, ophthalmic fibrosis, proliferative vitreoretinopathy; vitreoretinopathy of any etiology; fibrosis associated with retinal dysfunction; fibrosis associated with wet or dry macular degeneration; scarring in the cornea and conjunctiva; fibrosis in the corneal endothelium; anterior subcapsular cataract and posterior capsule opacification; anterior segment fibrotic diseases of the eye; fibrosis of the corneal stroma (e.g., associated with corneal opacification); fibrosis of the trabecular network (e.g., associated with glaucoma); posterior segment fibrotic diseases of the eye; fibrovascular scarring (e.g., in retinal or choroidal vasculature of the eye); retinal fibrosis; epiretinal fibrosis; retinal gliosis; subretinal fibrosis (e.g., associated with age related macular degeneration); tractional retinal detachment in association with contraction of the tissue in diabetic retinopathy; congenital orbital fibrosis; corneal subepithelial fibrosis; and Grave's ophthalmopathy.

Additional fibrotic disorders or fibrosis resulting from any one of the aforementioned conditions include, but are not limited to, spinal cord injury/fibrosis or central nervous system fibrosis such as fibrosis after a stroke, fibrosis associated with neurodegenerative disorder such as Alzheimer's disease or multiple sclerosis; vascular restenosis; uterine fibrosis; endometriosis; ovarian fibroids; Peyronie's disease; polycystic ovarian syndrome; disease related pulmonary apical fibrosis in ankylosing spondylitis; and fibrosis incident to microbial infections (e.g., bacterial, viral, parasitic, fungal etc.).

In certain embodiments, the fibrotic condition is not coincidental to a cancerous condition, i.e., is not a cancerous proliferative disorder, and does not include idiopathic arthrofibrosis, or dermatological scarring.

As used herein, treatment of fibrosis or fibrotic conditions is meant to include disruption of the fibrotic processes so as to halt progression of the fibrotic condition, slow progression of the fibrotic condition, or cause regression of the fibrotic condition (i.e., improve the patient's state of health with respect to the degree of fibrosis in the affected tissue or organ). In certain embodiments, where treatment precedes onset of the fibrotic condition, i.e., treatment is performed prior to a known or an otherwise expected onset of fibrosis, then such treatment may include preventing development or onset of the fibrotic condition.

In one embodiment, the fibrotic condition is treated with an effective amount of an LDH inhibitor in the absence of any other agents. In other words, the invention consists of administering the LDH inhibitor to the individual receiving such treatment, where such administering can be performed repeatedly over a period of time (including indefinitely) using any acceptable dosage schedule.

In another embodiment, the fibrotic condition is treated with an effective amount of an LDH inhibitor in the absence of particular agents such as anti-proliferative agents used in the treatment of cancer. In other words, the invention consists essentially of administering the LDH inhibitor to the individual receiving such treatment, where such administering can be performed repeatedly over a period of time (including indefinitely) using any acceptable dosage schedule. In this embodiment, additional agents can be administered to treat the fibrotic condition.

A number of LDH inhibitors are known in the art and can be used to practice the present invention.

In certain embodiments, the LDH inhibitor can take the form of an RNAi agent that reduces the expression (and, thus, activity) of LDH. These RNAi agents include siRNA, shRNA, miRNA and other antisense nucleic acids. These RNAi agents can be administered in a formulation or via gene therapy using known techniques.

The use of antisense methods to inhibit the in vivo translation of genes is well known in the art (e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,1796 to Cowsert et al., which are hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an RNA molecule (e.g., an mRNA molecule) (e.g., Weintraub, H. M., "Antisense DNA and RNA," Scientific Am. 262:40-46 (1990), which is hereby incorporated by reference in its entirety). The antisense nucleic acids hybridize to corresponding nucleic acids, such as mRNAs, to form a double-stranded molecule, which interferes with translation of the mRNA, as the cell will not translate a double-stranded mRNA. Antisense nucleic acids used in the invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense molecules directed to LDH nucleic acids, which are known in the art, are particularly suited for use in the methods of the present invention. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of an LDH mRNA sequence. siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. A number of siRNA molecules directed to interfering with LDH expression are known in the art. For example, a targeting sequence for LDHa was selected as described previously by Kim and Lee et al., *Appl.*

*Microbiol. Biotechnol.* 74(1):152-159 (2007) and the LDHa siRNA sequence CTCGATTCCGTTATCTGAT (SEQ ID NO:1) and its use are described in U.S. Application Publ. No. 20130084605, both of which are hereby incorporated by reference in its entirety). Additional targeting sequences are defined in U.S. Application Publ. No. 20140004565, which is hereby incorporated by reference in its entirety, and commercial siRNA products are available from Santa Cruz. These are suitable for use in the present invention. In addition, various improvements of siRNA compositions, such as the incorporation of modified nucleosides or motifs into one or both strands of the siRNA molecule to enhance stability, specificity, and efficacy, have been described and are suitable for use in accordance with this aspect (International Patent Publication No. WO 2004/015107 to Giese et al.; International Patent Publication No. WO 2003/070918 to McSwiggen et al.; International Patent Publication No. WO 1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. Like siRNA, they silence gene expression via the cellular RNA interference pathway. shRNA is cleaved by cellular machinery into siRNA. Suitable shRNA molecules for inhibiting LDH expression that can be used in accordance with the methods of the present invention include the LDHa-directed sequence $^{69}$GCCGAGAGCATAATGAAGAACCTTAGGCG (SEQ ID NO: 2), whose use for in vitro LDHa knockdown is reported in Newington et al., "Overexpression of Pyruvate Dehydrogenase Kinase 1 and Lactate Dehydrogenase A in Nerve Cells Confers Resistance to Amyloid 0 and Other Toxins by Decreasing Mitochondrial Respiration and Reactive Oxygen Species Production," *J. Biol. Chem.* 287: 37245-58 (2012), which is hereby incorporated by reference in its entirety.

Other examples of LDH inhibitors include, but are not limited to, oxamate, gossypol, galloflavin, 3-hydroxyisoxazole-4-carboxylic acid (HICA), 4-hydroxy-1,2,5-thiadiazole-3-carboxylic acid (HTCA), a derivative of 8-deoxyhemigossylic (2,3-dihydroxynaphtalen-1-carboxylic) acid, an N-hydroxyindole-based inhibitor (e.g., FX11), a bis[thiohydrazide amide] compound (e.g., elesclomol; see U.S. Patent Application Publication No. 20130150440, which is hereby incorporated by reference in its entirety).

Additional LDH inhibitors are disclosed in U.S. Patent Application Publication No. 20120309794, which is hereby incorporated by reference in its entirety. The disclosed LDH inhibitors have the structure according to formula (I) below:

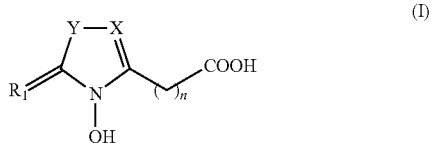

(I)

wherein:
n is selected from the group consisting of: 0, 1;
X is selected from the group consisting of: N, N$^+$—O$^-$, C—Z;
Y is selected from the group consisting of: S, O, C=R$^2$;

Z is selected from the group consisting of: hydrogen, OR$^A$, NR$^A$R$^B$, halogen, cyano, nitro, alkoxy, aryloxy, heteroaryloxy, —C(O)C$_{1-6}$-alkyl, —C(O)phenyl, —C(O)benzyl, —C(O)C$_{5-6}$-heterocycle, —S—C$_{1-6}$-alkyl, —S-phenyl, —S-benzyl, —S—C$_{5-6}$-heterocycle, —S(O)C$_{1-6}$-alkyl, —S(O)phenyl, —S(O)benzyl-S(O)$_2$C$_{5-6}$-heterocycle, —S(O)$_2$C$_{1-6}$-alkyl, —S(O)$_2$phenyl, —S(O)$_2$benzyl, —S(O)$_2$C$_{5-6}$-heterocycle, —S(O)$_2$NR$^A$R$^B$, C$_{1-6}$-alkyl, halo-C$_{1-6}$-alkyl, dihalo-C$_{1-6}$-alkyl, trihalo-C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, phenyl, benzyl, and C$_{5-6}$-heterocycle;
R$^1$ is selected from:

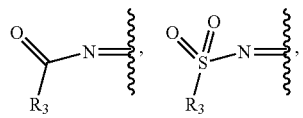

and R$^2$ together with R$^1$ is

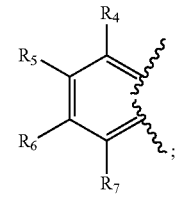

R$^3$ is selected from the group consisting of: hydrogen, C$_{1-4}$-alkyl, halo-C$_{1-4}$-alkyl, dihalo-C$_{1-4}$-alkyl, trihalo-C$_{1-4}$-alkyl, C$_{2-6}$-alkenyl, C$_{2-4}$-alkynyl, C$_{3-6}$-cycloalkyl, C$_{3-6}$-cycloalkyl-C$_{1-2}$-alkyl, phenyl, benzyl, and C$_{5-6}$-heterocycle;
R$^4$, R$^5$, R$^6$, R$^7$ are independently selected from the group consisting of: hydrogen, OR$^A$, NR$^A$R$^B$, —C(O)R$^A$, —C(O)OR$^A$, —C(O)NR$^A$R$^B$, halogen, cyano, nitro, alkoxy, aryloxy, heteroaryloxy, —C(O)C$_{1-6}$-alkyl, —C(O)phenyl, —C(O)benzyl, —C(O)C$_{5-6}$-heterocycle, —S—C$_{1-6}$-alkyl, —S-phenyl, —S-benzyl, —S—C$_{5-6}$-heterocycle, —S(O)C$_{1-6}$-alkyl, —S(O)phenyl, —S(O)benzyl, —S(O)C$_{5-6}$-heterocycle, —S(O)$_2$C$_{1-6}$-alkyl, —S(O)$_2$phenyl, —S(O)$_2$benzyl, —S(O)$_2$C$_{5-6}$-heterocycle, —S(O)$_2$NR$^A$R$^B$, C$_{1-6}$-alkyl, halo-C$_{1-6}$-alkyl, dihalo-C$_{1-6}$-alkyl, trihalo-C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, phenyl, benzyl, naphthyl, and C$_{5-6}$-heterocycle;
wherein the phenyl, benzyl, naphthyl and C$_{5-6}$ heterocycle of the R$^3$, R$^4$, R$^5$, R$^6$, R$^7$, R$^A$ or R$^B$ group may optionally be substituted with 1 to 3 groups independently selected from OR$^C$ wherein two OR$^C$ groups may concur into forming a cycle, NR$^C$R$^D$, —C(O)R$^C$, —C(O)OR$^C$, C$_{1-4}$-alkyl-OR$^C$, C$_{1-4}$-alkyl-C(O)OR$^C$, —C(O)NR$^C$R$^D$, —S(O)$_2$NR$^C$R$^D$, —S(O)$_2$C$_{1-6}$-alkyl, halogen, cyano, nitro, C$_{1-4}$-alkyl, halo-C$_{1-4}$-alkyl, dihalo-C$_{1-4}$-alkyl, trihalo-C$_{1-4}$-alkyl, aryl or heteroaryl optionally substituted with C(O)OR$^C$;
wherein any atom of the C$_5$-C$_6$ heterocycle of the R$^3$, R$^4$, R$^5$, R$^6$ and R$^7$ group may be bound to an oxygen so to form an oxo or a sulfoxo moiety;
wherein any alkyl, alkenyl and alkynyl groups of the R$^A$, R$^B$, R$^4$, R$^5$, R$^6$ or R$^7$ may optionally be substituted with 1-3 groups independently selected from OR$^C$, NR$^C$R$^D$, halogen, cyano and nitro;

wherein any carbon-bound hydrogen atom may be substituted with a fluorine atom;

$R^A$, $R^B$, $R^C$ and $R^D$ are independently selected from the group consisting of: hydrogen, —C(O)$C_{1-6}$-alkyl, —C(O)phenyl, —C(O)benzyl, —C(O)$C_{5-6}$-heterocycle, —S(O)$_2$$C_{1-6}$alkyl, —S(O)$_2$phenyl, —S(O)$_2$benzyl, —S(O)$_2$$C_{5-6}$-heterocycle, $C_{1-6}$-alkyl, halo-$C_{1-6}$-alkyl, dihalo-$C_{1-6}$-alkyl, trihalo-$C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, phenyl, benzyl, and $C_{5-6}$-heterocycle;

wherein the compounds of formula (I) are selective inhibitors of the LDH-A subunit of LDH enzymes, particularly LDH5. Salts and prodrugs of these compounds are also disclosed therein.

In certain embodiments, the compounds of formula (I) have the structure according to formula (Ia), (Ib)

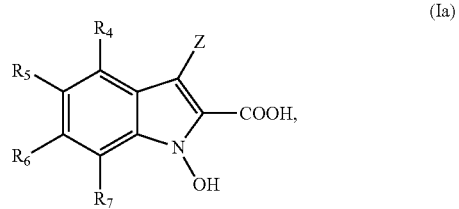

(Ib)

wherein in the compounds of formula (Ia), Z, $R^4$, $R^5$, $R^6$ and $R^7$ are defined as under formula (I) above; or wherein in the compounds of formula (Ib), Z is either H or a $C_{1-6}$ alkyl; $R^4$, $R^5$, $R^6$ and $R^7$ are as defined under formula (I) above, and such that at least one of $R^4$, $R^5$, $R^6$ and $R^7$ is selected from the list of trihalo-$C_{1-4}$-alkyl, —S(O)$_2$NR$^A$R$^B$, phenyl, naphthyl or $C_{5-6}$ heterocycle optionally substituted with 1 to 3 groups independently selected from OR$^C$, NR$^C$R$^D$, —C(O)R$^C$, —C(O)OR$^C$, $C_{1-4}$-alkyl-OR$^C$, $C_{1-4}$-alkyl-C(O)OR$^C$, —C(O)NR$^C$R$^D$, —S(O)$_2$NR$^C$R$^D$, —S(O)$_2$$C_{1-6}$-alkyl, halogen, cyano, nitro, $C_{1-4}$-alkyl, halo-$C_{1-4}$-alkyl, dihalo-$C_{1-4}$-alkyl, trihalo-$C_{1-4}$-alkyl, aryl or heteroaryl optionally substituted with C(O)OR$^C$, and wherein $R^A$, $R^B$, $R^C$ and $R^D$ are as defined under formula (I) above.

As used in the definitions of formulae (I), (Ia), and (Ib), the term "alkyl" encompasses all saturated hydrocarbons, whether linear or branched. Non-limiting examples include methyl, ethyl, n-propyl, iso-propyl, n-butyl, iso-butyl, t-butyl, sec-butyl, pentyl, hexyl, heptyl, octyl, nonyl, and decyl. Amongst the linear alkyls, methyl, ethyl, n-propyl and n-butyl are preferred. Non-limiting examples of branched alkyls include: t-butyl, i-butyl, 1-ethylpropyl, 1-ethylbutyl and 1-ethylpentyl.

As used in the definitions of formulae (I), (Ia), and (Ib), the term "alkoxy" encompasses O-alkyl groups, wherein alkyl is intended as described above. Non-limiting examples of alkoxy groups include methoxy, ethoxy, propoxy and butoxy.

As used in the definitions of formulae (I), (Ia), and (Ib), the term "alkenyl" encompasses unsaturated hydrocarbons, whether linear or branched, containing at least one carbon-carbon double bond. Alkenyl groups may, for example, contain up to five carbon-carbon double to bonds. Non-limiting examples of alkenyl groups include ethenyl, propenyl, butenyl, pentenyl, hexenyl, heptenyl, octenyl, nonenyl, decenyl and dodecenyl. Preferred alkenyl groups include ethenyl, 1-propenyl and 2-propenyl.

As used in the definitions of formulae (I), (Ia), and (Ib), the term "alkynyl" encompasses unsaturated hydrocarbons, whether linear or branched, containing at least one triple carbon-carbon bond. Alkynyl groups may, for example, contain up to five carbon-carbon triple bonds. Non-limiting examples of alkynyl groups include ethynyl, propynyl, butyryl, pentynyl, hexynyl, heptynyl, octynyl, nonynyl, decynyl and dodecynyl. Preferred alkynyl groups include ethynyl, 1-propynyl and 2-propynyl.

As used in the definitions of formulae (I), (Ia), and (Ib), the term "cycloalkyl" encompasses cyclic saturated hydrocarbons. Cycloalkyl groups may be either monocyclic or bicyclic. A bicyclic group may be fused or bridged. Non-limiting examples of cycloalkyl groups include cyclopropyl, cyclobutyl and cyclopentyl. Other non-limiting examples of monocyclic cycloalkyls are cyclohexyl, cycloheptyl and cyclooctyl. An example of a bicyclic cycloalkyl is bicyclo[2.2.1]-hept-1-yl. The cycloalkyl group is preferably monocyclic.

As used in the definitions of formulae (I), (Ia), and (Ib), the term "aryl" encompasses aromatic carbocyclic moieties which may be monocyclic or bicyclic.

Non-limiting examples of aryl groups are phenyl and naphthyl. A naphthyl group may be linked either via its 1- or its 2-position. In a bicyclic aromatic group, one of the rings may be saturated. Non-limiting examples of such rings include indanyl and tetrahydronaphtyl. More specifically, a "$C_{5-10}$ aryl" group encompasses monocyclic or bicyclic aromatic systems containing 5 to 10 carbon atoms. One preferred $C_{5-10}$ aryl group is phenyl.

As used in the definitions of formulae (I), (Ia), and (Ib), the term "aryloxy" encompasses O-aryl groups wherein aryl is intended as described above. A non-limiting example of an aryloxy group is the phenoxy group.

As used in the definitions of formulae (I), (Ia), and (Ib), the term "halogen" encompasses fluoro, chloro, bromo and iodo. Fluoro, chloro and bromo are particularly preferred.

As used in the definitions of formulae (I), (Ia), and (Ib), the term "haloalkyl" encompasses alkyl groups harboring a halogen substituent, wherein alkyl and halogen are intended as described above. Similarly, the term "dihaloalkyl" encompasses alkyl groups having two halogen substituents and the term "trihaloalkyl" encompasses alkyl groups harboring three halogen substituents. Non-limiting examples of haloakyl groups include fluoromethyl, chloromethyl, bromomethyl, fluoroethyl, fluoropropyl and fluorobutyl; non-limiting examples of dihaloalkyl groups are difluoromethyl and difluoroethyl; and non-limiting examples of trihaloalkyl groups are trifluoromethyl and trifluoroethyl.

As used in the definitions of formulae (I), (Ia), and (Ib), the term "heterocycle" encompasses aromatic ("heteroaryl") or non-aromatic ("heterocycloalkyl") carbocyclic groups wherein one to four carbon atoms is/are replaced by one or more heteroatoms selected from the list of nitrogen, oxygen and sulphur. A heterocyclic group may be monocyclic or bicyclic. Within a bicyclic heterocyclic group, one or more heteroatoms may be found on either ring or in one of the rings only. Wherein valence and stability permit, nitrogen-containing heterocyclic groups also encompass their respective N-oxides. Non-limiting examples of monocyclic heteroacycloalkyl include aziridinyl, azetidinyl, pyrrolidinyl, imidazolidinyl, pirazolidinyl, piperidinyl, piperazinyl, tetrahydrofuranyl, tetrahydropyranyl, morpholinyl, thiomorpholinyl and azepanyl.

As used in the definitions of formulae (I), (Ia), and (Ib), the term "$C_{5-10}$-heterocycle" encompasses a group containing 5 to 10 carbon atoms as part of a mono- or bicyclic ring system which can be aromatic ("heteroaryl") or non-aromatic ("heterocycloalkyl"), wherein one to four carbon atoms is/are replaced by one or more heteroatoms selected from the list of nitrogen, oxygen and sulphur. More precisely, the term "$C_5$-heterocycle" encompasses 5-membered cyclic aromatic ("heteroaryl") or non-aromatic ("heterocycloalkyl") groups containing one or more heteroatoms independently selected from the list of nitrogen, oxygen and sulphur, whereas the remaining atoms forming the 5-membered ring are carbon atoms. Non-limiting examples of $C_5$-heterocyclic groups include furanyl, thienyl, pyrrolyl, imidazolyl, oxazolyl, thiazolyl and their respective partially or fully saturated analogues such as dihydrofuranyl and tetrahydrofuranyl.

Non-limiting examples of bicyclic heterocyclic groups wherein one of the two rings is not aromatic include dihydrobenzofuranyl, indanyl, indolinyl, tetrahydroisoquinolyl, tetrahydroquinolyl and benzoazepanyl.

Non-limiting examples of monocyclic heteroaryl groups include furanyl, thienyl, pyrrolyl, oxazolyl, thiazolyl, imidazolyl, oxadiazolyl, thiadiazolyl, pyridyl, triazolyl, triazinyl, pyridazyl, pyrimidinyl, isothiazolyl, isoxazolyl, pyrazinyl, pyrazolyl and pyrimidinyl.

Non-limiting examples of bicyclic heteroaryl groups include quioxalinyl, quinazolinyl, pyridopyrazolinyl, benzoxazolyl, benzothienyl, benzoimidazolyl, naphthyridyl, quinolinyl, benzofuranyl, indolyl, benzothiazolyl, oxazolyl[4,5-b]pyridyl, pyridopyrimidinyl and isoquinolinyl.

As used in the definitions of formulae (I), (Ia), and (Ib), the term "cycloalkylalkyl" encompasses cycloalkyl-alkyl groups, wherein cycloalkyl and alkyl have the meaning above described, which are bound via the alkyl group.

As used in the definitions of formulae (I), (Ia), and (Ib), the term "heteroaryloxy" encompasses O-heteroaryl groups, wherein heteroaryl is intended as described above. Non-limiting examples of heteroaryloxy groups are furanyloxy, thienyloxy, and pyridinoxy.

As used in the definitions of formulae (I), (Ia), and (Ib), the term "heterocycloalkoxy" encompasses O-heterocycloalkyl groups wherein heterocycloalkyl is intended as described above. Non-limiting examples of heterocycloalkoxy groups are piperidinyloxy, tetrahydrofuranyloxy, tetrahydropyranyloxy.

Exemplary compounds of formulae (I), (Ia), or (Ib) include, without limitation:
6-(3-carboxyphenyl)-1-hydroxy-1H-indol-2-carboxylic acid;
5-(4-carboxy-1H-1,2,3-triazol-1-yl)-1-hydroxy-1H-indol-2-carboxylic acid;
6-[4-(2-carboxyethyl)-1H-1,2,3-triazol-1-yl]-1-hydroxy-1H-indol-2-carboxylic acid;
1-hydroxy-6-phenyl-4-trifluoromethyl-1H-indol-2-carboxylic acid;
1-hydroxy-4-(4-phenyl-1H-1,2,3-triazol-1-yl)-1H-indol-2-carboxylic acid;
1-hydroxy-6-[N-methyl-N-phenylsulfamoyl]-1H-indol-2-carboxylic acid;
1-hydroxy-5-phenyl-1H-indol-2-carboxylic acid;
1-hydroxy-6-(4-methoxyphenyl)-1H-indol-2-carboxylic acid;
1-hydroxy-6-phenyl-1H-indol-2-carboxylic acid;
1-hydroxy-6-(2H-tetrazol-5-yl)-1H-indol-2-carboxylic acid;
5-[4-(2-carboxyethyl)phenyl]-1-hydroxy-1H-indol-2-carboxylic acid;
4-[4-(3-carboxyphenyl)-1H-1,2,3-triazol-1-yl]-1-hydroxy-1H-indol-2-carboxylic acid;
6-[4-(2-carboxyethyl)phenyl]-1-hydroxy-1H-indol-2-carboxylic acid;
6-[4-(4-carboxyphenyl)-1H-1,2,3-triazol-1-yl]-1-hydroxy-1H-indol-2-carboxylic acid;
5-(3-carboxyphenyl)-1-hydroxy-1H-indol-2-carboxylic acid;
1-hydroxy-5,6-diphenyl-1H-indole-2-carboxylic acid;
1-hydroxy-6-(N-methyl-N-p-tolylsulfamoyl)-1H-indole-2-carboxylic acid;
1-hydroxy-6-(N-methyl-N-(4-(trifluoromethyl)phenyl)sulfamoyl)-1H-indole-2-carboxylic acid;
6-(N-(4-fluorophenyl)-N-methylsulfamoyl)-1-hydroxy-1H-indole-2-carboxylic acid;
6-(N-(4-chlorophenyl)-N-methylsulfamoyl)-1-hydroxy-1H-indole-2-carboxylic acid;
5-(4-(3-carboxyphenyl)-1H-1,2,3-triazol-1-yl)-1-hydroxy-1H-indole-2-carboxylic acid;
1-hydroxy-6-(4-(trifluoromethyl)phenyl)-1H-indole-2-carboxylic acid;
6-(4-fluorophenyl)-1-hydroxy-1H-indole-2-carboxylic acid;
5-(4-fluorophenyl)-1-hydroxy-1H-indole-2-carboxylic acid;
1-hydroxy-5-(4-(trifluoromethyl)phenyl)-1H-indole-2-carboxylic acid;
6-(benzo[d][1,3]dioxol-5-yl)-1-hydroxy-1H-indole-2-carboxylic acid;
1-hydroxy-5-(4-methoxyphenyl)-1H-indole-2-carboxylic acid;
6-(N-(2-chlorophenyl)-N-methylsulfamoyl)-1-hydroxy-1H-indole-2-carboxylic acid;
6-(2,2-difluorobenzo[d][1,3]dioxol-5-yl)-1-hydroxy-1H-indole-2-carboxylic acid;
5-(4-chlorophenyl)-1-hydroxy-1H-indole-2-carboxylic acid;
6-(4-chlorophenyl)-1-hydroxy-1H-indole-2-carboxylic acid;
1-hydroxy-6,7-diphenyl-4-(trifluoromethyl)-1H-indole-2-carboxylic acid
6-(N-butyl-N-phenylsulfamoyl)-1-hydroxy-1H-indole-2-carboxylic acid;
6-(4-(N,N-dimethylsulfamoyl)phenyl)-1-hydroxy-1H-indole-2-carboxylic acid;
6-(furan-3-yl)-1-hydroxy-1H-indole-2-carboxylic acid;
1-hydroxy-6-(3-(trifluoromethoxy)phenyl)-1H-indole-2-carboxylic acid;
6-(4-chlorophenyl)-1-hydroxy-4-(trifluoromethyl)-1H-indole-2-carboxylic acid;
6-(biphenyl-4-yl)-1-hydroxy-1H-indole-2-carboxylic acid;
1-hydroxy-3-methyl-6-phenyl-4-(trifluoromethyl)-1H-indole-2-carboxylic acid;
1-hydroxy-6-(4-(trifluoromethoxy)phenyl)-1H-indole-2-carboxylic acid);
1-hydroxy-6-(4-(N-methyl-N-phenylsulfamoyl)phenyl)-1H-indole-2-carboxylic acid;
6-(4-chlorophenyl)-1-hydroxy-3-methyl-4-(trifluoromethyl)-1H-indole-2-carboxylic acid;
1-hydroxy-6-(naphthalen-1-yl)-1H-indole-2-carboxylic acid;
1-hydroxy-6-(naphthalen-2-yl)-1H-indole-2-carboxylic acid;
6-(2,4-dichlorophenyl)-1-hydroxy-4-(trifluoromethyl)-1H-indole-2-carboxylic acid;
6-(N-(3-chlorophenyl)-N-methylsulfamoyl)-1-hydroxy-1H-indole-2-carboxylic acid; and
1-hydroxy-5-(N-methyl-N-phenylsulfamoyl)-1H-indole-2-carboxylic acid.

Other known LDH inhibitors may also include N-isopropyl oxamate, and their pharmaceutically acceptable salts, a 1,4-dihydropyridine or a pharmaceutically acceptable salt thereof, oxalic acid or a pharmaceutically acceptable salt thereof, pyruvic acid or a pharmaceutically acceptable salt thereof, malonic acid or a pharmaceutically acceptable salt thereof, tartronic acid or a pharmaceutically acceptable salt thereof, ethylenediaminetetraacetic acid or a pharmaceutically acceptable salt thereof, iodoacetamide or a pharmaceutically acceptable salt thereof, an iodide, and a silver salt. See U.S. Patent Application Publication No. 20050014692, which is hereby incorporated by reference in its entirety.

Alternative LDH inhibitors derived from herbal extracts include, without limitation, 2'3,4'5,7-pentahydroxyflavone (morin), epigallocatechin gallate, quercetin, citric acid, rosemary (*Rosemarinus officinalis*), black walnut (*Juglans nigra*), clove (*Syzygium aromaticum*), nutmeg (*Myristica fragans*), licorice root (*Glycyrrhiza glabra*), coriander (*Coriandrum sativum*), cinnamon (*Cinnamomum cassia*), ginger root (*Zingiber officinale*), myrrh gum (*Commiphora molmol*), and green tea (*Camellia sinensis*). See U.S. Patent Application Publication Nos. 20060035981, 20070248693, 20100209388, each of which is hereby incorporated by reference in its entirety.

In certain embodiments, the LDH inhibitor is an LDH5 inhibitor, which may or may not be a selective LDH5 inhibitor. RNAi against LDH5, the LDH inhibitors of formulae (I), (Ia), and (Ib), and gossypol represent non-limiting examples of LDH5 inhibitors.

The LDH inhibitors can be administered to an individual in the form of a pharmaceutically acceptable dosage unit that includes an effective amount of the active agent and a pharmaceutically acceptable carrier. Typically, the therapeutic agent will be administered to a mammal as a pharmaceutical formulation that includes the therapeutic agent and any pharmaceutically acceptable suitable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of therapeutic agent together with the adjuvants, carriers, and/or excipients. The amount of active compound in such therapeutically useful compositions is such that a suitable dosage unit will be obtained.

The dosage of the LDH inhibitor is preferably administered at a dose of between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day.

Administration can be accomplished either via systemic administration to the subject, administration directly to a fibrotic tissue site, or via targeted administration to affected cells. Exemplary routes of administration include, without limitation, orally, parenterally, periadventitially, subcutaneously, intravenously, intramuscularly, intraperitoneally, by inhalation, by intranasal instillation, by implantation, by intracavitary or intravesical instillation, intraocularly, intraarterially, intralesionally, transdermally, intradermally or by application to mucous membranes. Other suitable modes of delivery can also be used.

As persons of skill will recognize, optimization of dosage amount and frequency can be carried out to maximize the efficacy of treatment in accordance with the present invention.

The agents may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of the agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

The agents may also be administered parenterally. Solutions or suspensions of the agent can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

As another alternative, the agents of the present invention may be administered to the airways in the form of a lung surfactant formulation. The lung surfactant formulation can include exogenous lung surfactant formulations (e.g., INFASURF® (Forest Laboratories), SURVANTA® (Ross Products), and CUROSURF® (DEY, California, USA) or synthetic lung surfactant formulations (e.g., Exosurf (GlaxoWellcome Inc.) and ALEC). These surfactant formulations are typically administered via airway instillation (i.e., after intubation) or intratracheally.

The agents of the present invention may be administered directly to the targeted tissue. Additionally and/or alternatively, the agent may be administered to a non-targeted area along with one or more agents that facilitate migration of the agent to (and/or uptake by) a targeted tissue, organ, or cell. As will be apparent to one of ordinary skill in the art, the therapeutic agent itself can be modified to facilitate its transport to (and uptake by) the desired tissue, organ, or cell.

Exemplary delivery devices include, without limitation, nebulizers, atomizers, liposomes, transdermal patches, implants, implantable or injectable depot compositions, syringes, and gene therapy. Other delivery systems which are known to those of skill in the art can also be employed to achieve the desired delivery of the therapeutic agent to the desired organ, tissue, or cells in vivo to carry out this aspect of the present invention.

In certain embodiments, the administration of the LDH inhibitor is effective to inhibit TGF-β-induced myofibroblast differentiation, inhibit pro-fibrotic gene expression (e.g., one or more of collagen I, fibronectin ("FN"), a smooth muscle actin ("αSMA"), and calponin), and/or inhibit lactic acid production that reduces extracellular pH.

As noted above, in certain embodiments it is contemplated that the LDH inhibitor can be used in combination with one or more additional therapeutic agents that are effective for treating the fibrotic condition (i.e., additional anti-fibrotic agents).

Exemplary additional anti-fibrotic agents include, without limitation, calcium channel blockers, cytotoxic agents, cytokines, chemokines, integrins, growth factors, hormones, lysophosphatidic acid ("LPA") receptor 1 antagonists, agents that modulate the TGF-β pathway, endothelin receptor antagonists, agents that reduce connective tissue growth factor ("CTGF") activity, matrix metalloproteinase ("MMP") inhibitors, agents that reduce the activity of platelet-derived growth factor ("PDGF"), agents that interfere with integrin function, agents that interfere with the pro-fibrotic activities of cytokines, agents that reduce oxidative stress, PDE4 inhibitors, PDE5 inhibitors, mTor inhibitors, modifiers of the arachidonic acid pathway, peroxisome proliferator-activated receptor ("PPAR")-γ agonists, kinase inhibitors, inhibitors of VEGF signaling pathway, matrix metalloproteinases, tissue inhibitors of metalloproteinases ("TIMPs"), HGF agonists, angiotensin-converting enzyme ("ACE") inhibitors, angiotensin receptor antagonists, inhibitors of advanced glycation endproducts ("AGEs") or their receptors ("RAGEs"), Rho kinase inhibitors, PKC inhibitors, ADAM-10 inhibitor, farnesoid X receptor agonists, caspase inhibitors, anti-oxidants, inhibitors of collagen expression, LMW heparin or heparin analogs, copper chelators, TNF-α blocking agents, agents that inhibit fibronectin deposition and/or enhance fibronectin degradation and turnover (e.g., bacterial adhesin peptides, fibronectin-derived peptides, and antibodies against fibronectin, as described in U.S. Appl. Publ. No. 20130190224 to Sottile et al., which is hereby incorporated by reference in its entirety), HMG-CoA reductase inhibitors, and Thy-1 (CD90) inhibitors.

Exemplary calcium channel blockers include, without limitation, Verapamil.

Exemplary cytotoxic agents include, without limitation, azathioprine, methotrexate, and cyclophosphamide. In certain embodiments, these agents can be excluded.

Exemplary cytokines include, without limitation, interleukins such as IL-1, IL-4, IL-5, IL-6, IL-8, IL-10, IL-12, and IL-13; interferons such as interferon-γ; lymphokines; tumor necrosis factor-α; endothelin-1; angiotensin II; leptins; angiogenin(s); monocyte chemoattractant protein type 1 (MCP-1); and macrophage inflammatory protein (MIP-1α, MIP-2).

Exemplary chemokines include, without limitation, CCL2, CCL12, CXCL12, CXCR4, CCR3, CCR5, CCR7, and SLC/CCL21.

Exemplary integrins include, without limitation, $\alpha_1\beta_1$, $\alpha_2\beta_1$, $\alpha_v\beta_6$, and $\alpha_v\beta_3$.

Exemplary growth factors include, without limitation, insulin growth factors (IGF-1, IGF-2), keratinocyte growth factor ("KGF"), hepatocyte growth factor ("HGF"), fibroblast growth factors (FGF-1, 2 and 4), platelet-derived growth factors (PDGF-AB, PDGF-BB, PDGF-AA), epidermal growth factors ("EGFs"), transforming growth factors (TGF-β1-3), osteoid-inducing factor ("OIF"), bone morphogenic proteins (BMPs; BMP1, BMP2, BMP2A, BMP2B, BMP3, BMP3b, BMP4, BMP5, BMP6, BMP9-BMP-15, OP-1, OP-2, OP-3, BMP-7, HBGF-1, HBGF-2), growth differentiation factors (GDF1-3 and GDF5-12), osteogenic proteins (OP-1, OP-2, OP-3), cartilage-derived morphogenic proteins (CDMP-1, CDMP-2, CDMP-3), colony stimulating factors (CSF-1, G-CSF and GM-CSF or isoforms thereof), vascular endothelial growth factor ("VEGF"), connective tissue growth factor ("CTGF"), and neural epidermal growth factor-like 1 (NELL-1).

Exemplary hormones include, without limitation, progesterone, estrogen, testosterone, growth hormone, thyroid hormone, and parathyroid hormone.

Exemplary lysophosphatidic acid (LPA) receptor 1 antagonists include, without limitation, AM152 (Amira Pharmaceuticals), AM966, and Ki16198.

Exemplary agents that modulate TGF-β pathways include, without limitation, $\alpha_v\beta_6$ inhibitors; HGF; rBMP7 (bone morphogenic protein 7); decorin; tyrosine kinase inhibitors (Imantinib, Desatinib, Nolitinib); and agents that that reduce TGF-β activity (e.g., metelimumab (CAT-192), GC-1008 (Genzyme/Medimmune), lerdelimumab (CAT-152), LY-2157299 (Eli Lilly), and ACU-HTR-028 (Opko Health)); antibodies that target one or more TGF-β isoforms; inhibitors of TGF-β receptor kinases (e.g., TGFBR1 (ALK5) and TGFBR2); modulators of post-receptor signaling pathways; and chemokine receptor signaling.

Exemplary endothelin receptor antagonists (including inhibitors that target both endothelin receptor A and B and those that selectively target endothelin receptor A) include, without limitation, ambrisentan; avosentan; bosentan; clazosentan; darusentan; BQ-153; FR-139317, L-744453; macitentan; PD-145065; PD-156252; PD163610; PS-433540; S-0139; sitaxentan sodium; TBC-3711; and zibotentan.

Exemplary agents that reduce the activity of connective tissue growth factor (CTGF) include, without limitation, FG-3019, FibroGen, other CTGF-neutralizing antibodies.

Exemplary matrix metalloproteinase (MMP) inhibitors include, without limitation, MMPI-12, PUP-1 and tigapotide triflutate.

Exemplary agents that reduce the activity of platelet derived growth factor ("PDGF") include, without limitation, Imatinib mesylate (Novartis)) and PDGF neutralizing antibodies, antibodies targeting PDGF receptor ("PDGFR"), inhibitors of PDGFR kinase activity, and post-receptor signaling pathways. PDGFR inhibitors include, but are not limited to, SU9518, CP-673,451 and CP-868596.

Exemplary agents that interfere with integrin function include, without limitation, STX-100, IMGN-388, and integrin targeted antibodies.

Exemplary agents that interfere with the pro-fibrotic activities of cytokines (such as interleukins, e.g., IL4 and IL-13) include, without limitation, AER-001, AMG-317, APG-201, sIL-4Rα, anrukinzumab, CAT-354, cintredekin besudotox, MK-6105, QAX-576, SB-313, SL-102, and TNX-650; as well as neutralizing antibodies to either cytokine, antibodies that target IL-4 receptor or IL-13 receptor, the soluble form of IL-4 receptor or derivatives thereof that is reported to bind and neutralize both IL-4 and IL-13, chimeric proteins including all or part of IL-13 and a toxin particularly pseudomonas endotoxin, signaling though the JAK-STAT kinase pathway.

Exemplary agents that interfere with epithelial mesenchymal transition include, without limitation, inhibitors of mTor (including but not limited to rapamycin, 40-O-(2-hydroxy)-ethyl-rapamycin, 32-deoxorapamycin, 40-[3-hydroxy-2-(hydroxy-methyl)-2-methylpropanoate]-rapamycin, Ridaforolimus (AP-23573 or MK-8669) and Torisel (temsirolimus).

Exemplary agents that reduce oxidative stress include, without limitation, N-acetylcysteine (a cysteine pro-drug), tetrathiomolybdate, and interferon-γ.

Exemplary agents that are inhibitors of phosphodiesterase 4 (PDE4) or phosphodiesterase 5 ("PDE5") include, without limitation, Roflumilast, mirodenafil, PF-4480682, sildenafil citrate, SLx-2101, tadalafil, udenafil, UK-369003, vardenafil, and zaprinast.

Exemplary modifiers of the arachidonic acid pathway include, with limitation, cyclooxygenase ("COX") and 5-lipoxygenase ("LO") inhibitors such as Zileuton.

Exemplary compounds that reduce tissue remodeling during fibrosis include, without limitation, prolyl hydrolase inhibitors such as 1016548, CG-0089, FG-2216, FG-4497, FG-5615, FG-6513, fibrostatin A (Takeda), lufironil, P-1894B, and safironil.

Exemplary PPAR-gamma agonists include, without limitation, pioglitazone (Takeda), farglitizar (GSK) and rosiglitazone (GSK).

Exemplary kinase inhibitors include, without limitation, MEK inhibitors (e.g., PD325901, ARRY-142886, ARRY-438162 and PD98059); EGFR inhibitors (e.g., Iressa™ (gefitinib, AstraZeneca), Tarceva™ (erlotinib or OSI-774, OSI Pharmaceuticals Inc.), Erbitux™ (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFR immunoliposomes (Hermes Biosciences Inc.) and combinations thereof, antibodies targeting EGF receptor, inhibitors of EGF receptor kinase, and modulators of post-receptor signaling pathways); ErbB2 receptor inhibitors (e.g., CP-724-714, CI-1033 (canertinib), Herceptin™ (trastuzumab), Omnitarg™ (2C4, petuzumab), TAK-165, GW-572016 (Ionafarnib), GW-282974, EKB-569, PI-166, dHER2 (HER2 Vaccine), APC8024 (HER2 Vaccine), anti-HER/2neu bispecific antibody, B7.her2IgG3, AS HER2 trifunctional bispecific antibodies, mAB AR-209 and mAB 2B-1); IGFIR antibodies (e.g., those described in PCT Application Publ. No. WO 2002/053596, which is hereby incorporated by reference in its entirety); AXL inhibitors (e.g., SGI-AXL-277 (SuperGen) as well as inhibitors disclosed in U.S. Pat. Pub. 20050186571, which is hereby incorporated by reference in its entirety); p38 inhibitors (e.g., SB202190, SB203580 and pyridinyl imidazoles); FGFR inhibitors (e.g., PD 17034, PD166866, and SU5402); TIE2 inhibitors (e.g., those described in Kissau, L. et. al., J Med Chem., 46:2917-2931 (2003), which is hereby incorporated by reference in its entirety); the following kinase inhibitors: Pan ERBB receptor inhibitors (e.g., GW572016, CI-1033, EKB-569, and Omnitarg), MP371 (SuperGen) which is an inhibitor of c-Kit, Ret, PDGFR, and Lck, as well as the non-receptor tyrosine kinase c-src, MP470 (SuperGen) which is an inhibitor of c-Kit, PDGFR, and c-Met, Imatinib (Gleevec™) which is an inhibitor of c-kit, PDGFR, and ROR, as well as the non-receptor tyrosine kinase bcl/abl, Lapatinib (Tykerb™) which is an epidermal growth factor receptor (EGFR) and ERBB2 (Her2/neu) dual tyrosine kinase inhibitor, inhibitors of PDGFR and VEGFR (e.g., Nexavar™ (sorafenib, BAY43-9006), Sutent™ (sunitinib, SU11248), and ABT-869), inhibitors of VEGFR and (e.g., Zactima™ (vandetanib, ZD-6474), BMS-690514 which is a reversible oral inhibitor of epidermal growth factor receptor ("EGFR/HER-1"), HER-2 and -4, and vascular endothelial growth factor receptors ("VEGFRs")-1 to -3, BIBF-1120 which is a receptor kinase inhibitor for VEGF, FGF and PDGF; inhibitors of the VEGF signaling pathway (e.g., PTC-299, INGN-241, oral tetrathiomolybdate, 2-methoxyestradiol, 2-methoxyestradiol nanocrystal dispersion, bevasiranib sodium, PTC-299, Veglin, VEGF neutralizing antibodies, soluble form of VEGFR1 (sFlt) and derivatives thereof which neutralize VEGF, anti-KDR antibodies, VEGFR1 (Flt1) antibodies (e.g., icrucumab (IMC-18F1)), VEGFR2 (KDR) antibodies (e.g., CDP-791 or IMC-1121B (ramucirumab) and VEGFR3 antibodies (e.g., mF4-31C1 from Imclone Systems) and CT-322 (Angiocept™; a VEGFR2 inhibitor), VEGF inhibitors (e.g., bevacizumab (Avastin™), pegaptanib, ranibizumab, NEOVASTAT™, AE-941, VEGF Trap, and PI-88), and VEGF receptor antagonists (e.g., JNJ-17029259 (4-[4-(1-Amino-1-methyl-ethyl)phenyl]-2-[4-(2-morpholin-4-yl-ethyl)phenylamino] pyrimidine-5-carbonitrile (a VEGF-R2 inhibitor)), PTK-787/ZK222584 (Astra-Zeneca), SU5416, SU11248 (Pfizer), ZD6474 ([N-(4-bromo-2-fluorophenyl)-6-methoxy-7-[(1-methylpiperidin-4-yl)methoxy]quinazolin-4-amine]), vandetanib, cediranib, AG-013958, CP-547632, E-7080 (lenvatinib), XL-184, L-21649, ZK-304709, SU6668, sorafenib, sunitinib, pazopanib, vatalanib, AEE-788, AMG-706 (motesanib), axitinib, BIBF-1120, SU-14813, XL-647, XL-999, ABT-869, BAY-57-9352, BAY-73-4506 (regorafinib), BMS-582664, CEP-7055, CHIR-265, OSI-930, TKI-258, fenretinide, and squalamine).

Suitable matrix degrading enzymes include those described in U.S. Application Publ. Nos. 20100003237 and 20120101325, each of which is hereby incorporated by reference in its entirety. Exemplary matrix degrading enzymes include, without limitation, pancreatic elastase, elastase-2a, elastase-2b, neutrophil elastase, proteinase-3, endogenous vascular elastase, cathepsin G, mast cell chymase, mast cell tryptase, plasmin, thrombin, granzyme B, cathepsin S, cathepsin K, cathepsin L, cathepsin B, cathepsin C, cathepsin H, cathespin F, cathepsin G, cathepsin O, cathepsin R, cathepsin V (cathepsin 12), cathepsin W, calpain 1, calpain 2, legumain, cathepsin Z (cathepsin X), cathepsin D, cathepsin E, chondroitinase ABC, chondroitinase AC, hyaluronidase, chymopapain, chymotrypsin, collagenase, papain, subtilisin, subtilisin A, heparanase. and matrix metalloproteinases, such as for example, MMP-1 (collagenase-1), MMP-2 (gelatinase A), MMP-3 (stromelysin-1), MMP-7 (matrilysin; PUMP1), MMP-8 (collagenase-2), MMP-9 (gelatinase B), MMP-10 (stromelysin-2), MMP-11 (stromelysin-3), MMP-12 (metalloelastase), MMP-13

(collagenase-3), MMP-14 (MT1-MMP), MMP-15 (MT2-MMP), MMP-16 (MT3-MMP), MMP-17 (MT4-MMP), MMP-18 (collagenase-4), MMP-19 (stromelysin-4), MMP-20 (enamelysin), MMP-21 (x-MMP), MMP-23A (MT5-MMP), MMP-23B, MMP-24 (MT5-MMP), MMP-25 (MT6-MMP), MMP-26 (matrilysin-2), MMP-27 (MMP-22; c-MMP), MMP-28 (epilysin), ADAMTS-1, ADAMTS-2, ADAMTS-3, ADAMTS-4 (aggrecanase-1), ADAMTS-5 (aggrecanase-2), ADAMTS-14.

Exemplary tissue inhibitors of matrix-metalloproteinases (TIMPs) include, without limitation, TIMP-1, TIMP-2, TIMP-3, and TIMP-4.

Exemplary HGF agonists include, without limitation, Refanalin (Angion Biomedica).

Exemplary ACE inhibitors include, without limitation, Alacepril, Benazepril, Captopril, Cilazapril, Ceronapril, Delapril, Enalapril, Enalaprilat, Fosinopril, Fosinoprilat, Imidapril, Lisinopril, Moexipril, Perindopril, Perindoprilat, Quinapril, Quinaprilat, Ramipril, saralasin acetate, spirapril, temocapril, trandolapril, fasidotrilat, beclometasone dipropionate, FPL-66564, Idrapril, MDL-100240, and S-5590.

Exemplary angiotensin receptor antagonists include, without limitation, Candesartan, Irbesartan, Losartan, Valsartan, Telmisartan, and Eprosartan.

Exemplary advanced glycation endproducts (AGEs) inhibitors include, without limitation, Pyridoxamine (Biostratum). Examples of AGE receptors (RAGE) inhibitors include, without limitation, TTP-488 (Transtech Pharma) and TTP-4000 (Transtech Pharma).

Exemplary Rho kinase inhibitors include, without limitation, GSK269962, GSK429286, AS 1892802, SB772077B, and SR3677.

Exemplary PKC inhibitors include, without limitation, Ruboxistaurin mesilate hydrate (Lilly).

Exemplary ADAM-10 inhibitors include, without limitation, XL-784 (Exelixis).

Exemplary farnesoid X receptor agonists include, without limitation, INT-747 (Intercept Pharmaceuticals).

Exemplary caspase inhibitors include, without limitation, PF-3491390 (Pfizer, formally IDN-6556), and LB84318 (LG Life Sciences).

Exemplary anti-oxidants include, without limitation, Heptax (Hawaii Biotech), N-acetylcysteine (Pierre Fabre), tocopherol, silymarin, and Sho-saiko-To (H-09).

Exemplary inhibitors of collagen expression include, without limitation, Pirfenidone (InterMune), Halofuginone (Collgard) and F351 (Shanghai Genomics).

Exemplary low molecular weight heparin or heparin analogs include, without limitation, Sulodexide (Keryx).

Exemplary copper chelators include, without limitation, Trientine (Protemix), Coprexa (Pipex), and tetrathiomolybdate.

Exemplary TNF-α blocking agents include, without limitation, Etanercept (Enbrel™) and pentoxyfylline (Trental™).

Exemplary HMG-CoA reductase inhibitors include, without limitation, statins such atorvastatin (Lipitor), fluvastatin (Lescol), lovastatin (Mevacor, Altocor), pitavastatin (Livalo), pravastatin (Pravachol), rosuvastatin (Crestor), and simvastatin (Zocor).

Exemplary Thy-1 (CD90) inhibitors include monoclonal antibodies against Thy-1 (e.g., clone 5E10, Gundlach et al., Bioconjug. Chem. 22(8):1706-14 (2011), which is hereby incorporated by reference in its entirety).

Other known anti-fibrotic agents include, without limitation, 5-flurouracil (5-FU; a pyrimidine analog), mitomycin C (MMC), colchicine (antibiotic), d-penicillamine, Pediapred oral liquid, Medrol, cyclosporine (an immunosuppressant), mycophenolate mofetil (MMF; Cellcept; an immunosuppressant); prednisolone; bovine collagen type I, ribavirin (a guanosine (ribonucleic) analog), spirichostatin A (a histone deacetylase inhibitor); TGF-2 specific inhibitors (transglutaminase-2), tacrolimus (FK5-6, a calcineurin inhibitor), relaxin, taurine, niacin, treprostinil (a prostacyclin analog), Tiplaxtinin (PAI-039, a plasminogen activator-1 inhibitor); Pentraxin-1 (e.g., serum amyloid P component (SAP), c-reactive protein (CRP), and PTX-3) and Pentraxin-2 (PTX-2 or PRM-151), imidazolium and imidazolinium salts (U.S. Publication Application No. 20116178040, which is hereby incorporated by reference in its entirety) and IL-17 antagonists (U.S. Publication Application No. 20110091378, which is hereby incorporated by reference in its entirety); relaxin (a hormone; U.S. Publication Application No. 20120101325, which is hereby incorporated by reference in its entirety), ultraviolet A (UVA), and cannabinoids and agents altering the MMP-TIMP balance.

These additional anti-fibrotic agents can be administered in any previously known dosage. Compositions including these agents preferably contain from about 0.01 to about 99 weight percent, more preferably from about 2 to about 60 weight percent, of therapeutic agent together with the adjuvants, carriers, and/or excipients. The amount of active compound in such therapeutically useful compositions is such that a suitable dosage unit will be obtained. The dosage of the one of these additional anti-fibrotic agents is preferably administered at a dose of between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day.

Administration of one or more of the additional anti-fibrotic agents (or compositions containing the same) can be carried out orally, parenterally, periadventitially, subcutaneously, intravenously, intramuscularly, intraperitoneally, by inhalation, by intranasal instillation, by implantation, by intracavitary or intravesical instillation, intraocularly, intraarterially, intralesionally, transdermally, intradermally or by application to mucous membranes. Other suitable modes of delivery can also be used.

A further aspect relates to the above-identified combination therapies contemplated herein. In this aspect, a pharmaceutical composition or system is provided that includes therapeutically effective amounts of both the LDH inhibitor and the at least one additional anti-fibrotic agent, each in a pharmaceutically acceptable carrier.

In one embodiment, the LDH inhibitor and the at least one additional anti-fibrotic agent are both present in the same carrier (i.e., present in the form of a single composition).

In one embodiment, the LDH inhibitor and the at least one additional anti-fibrotic agent are both present in in separate carriers (i.e., each is present in the form of a distinct composition). In this embodiment, the two distinct compositions are capable of use together, either with contemporaneous co-administration or separate administration according to distinct protocols specific for each composition.

Regardless of the embodiment, these compositions of the present invention are suitable for use according to the same modes of delivery described above, and are intended for inclusion with suitable carriers, excipients, and additives as is well known in the art.

EXAMPLES

The following examples are intended to illustrate practice of the invention, and are not intended to limit the scope of the claimed invention.

Materials and Methods for Examples 1-4

Cells and reagents: Healthy and fibrotic human lung fibroblasts were derived from tissue explants as described (Baglole et al., "Isolation and Phenotypic Characterization of Lung Fibroblasts," *Methods Mol. Med.* 117:115-127 (2005) and Ferguson et al., "Electrophilic Peroxisome Proliferator-Activated Receptor-Gamma Ligands Have Potent Antifibrotic Effects in Human Lung Fibroblasts," *Am. J. Respir. Cell Mol. Biol.* 41:722-730 (2009), which are hereby incorporated by reference in their entirety). Informed written consent was obtained from all donors and the collection protocol was approved by the University of Rochester Institutional Review Board. TGF-b (R&D Systems, Minneapolis, Minn.) and gossypol (Cayman, Ann Arbor, Mich.) were added to the media at the concentrations indicated in the figure legends, and cells were harvested after 24-72 hours as indicated in the figure legends.

LDH assay: Cell lysates were collected as above and subsequently incubated in the presence of the working buffer containing 0.05M Potassium Phosphate pH 7.5, 30 mM pyruvic acid, and 0.25 mM β-NADH with and without gossypol at 1 mM, 5 mM, and 10 mM concentrations for 15 minutes. The LDH activity was assessed using spectrophotometry using the millimolar extinction coefficient of NADH of 6.33.

Alamar blue assay: Fibroblasts were cultured with and without TGF-β and/or gossypol for 72 hours and subsequently incubated with Alamar blue (Invitrogen, Grand Island, N.Y.). Alamar blue incorporation was determined by spectrophotometric analysis per the manufacturer's protocol.

Lactate assay: Lactate was measured in the supernatants using a commercially available assay kit (BioVision Inc, Milpitas, Calif.). Fibroblasts were cultured with and without TGF-β and/or gossypol for 72 hours to allow for the induction of myofibroblast differentiation. Supernatants were collected and analyzed for lactate concentrations per the manufacturer's protocol.

Western blot: Cell lysates were analyzed on SDS-PAGE and examined for expression of αSMA (Sigma Aldrich, St. Louis, Mo.), calponin (Dako, Carpinteria, Calif.), LDHA (Abcam, Cambridge, Mass.) by western blot as previously described (Ferguson et al., "Electrophilic Peroxisome Proliferator Activated Receptor-{gamma} (PPAR{gamma}) Ligands have Potent Anti-fibrotic Effects in Human Lung Fibroblasts," *Am. J. Respir. Cell Mol. Biol.* 41(6):722-30 (2009), which is hereby incorporated by reference in its entirety). GAPDH (Abcam, Cambridge, Mass.) and β-tubulin (Abcam, Cambridge, Mass.) were utilized as loading controls.

TGF β bioactivity assay: Mv1Lu mink lung epithelial cells (American Type Culture Collection CCl-64) were cultured in 96-well plates as previously described (Jurukovski et al., "Methods for Measuring TGF-b Using Antibodies, Cells, and Mice," *Methods Mol. Med.* 117:161-175 (2005), which is hereby incorporated by reference in its entirety). The Mv1Lu cells were cultured for 12 hours with conditioned media from fibroblasts treated with TGF-β and/or gossypol. [3H]Thymidine (1 μCi/well) was added and the cells were incubated for a further 4 hours. Incorporation was measured with a Topcount Luminometer (PerkinElmer, Boston, Mass.).

qRT-PCR: RNA was isolated from primary human lung fibroblast cultures as previously described (Ferguson et al., "Electrophilic Peroxisome Proliferator Activated Receptor-{gamma} (PPAR{gamma}) Ligands have Potent Anti-fibrotic Effects in Human Lung Fibroblasts," *Am. J. Respir. Cell Mol. Biol.* 41(6):722-30 (2009), which is hereby incorporated by reference in its entirety). qRT-PCR reactions were performed for COL1A and COL3A1 and compared to GAPDH as previously described (Ferguson et al., "Electrophilic Peroxisome Proliferator-Activated Receptor-Gamma Ligands Have Potent Antifibrotic Effects in Human Lung Fibroblasts," *Am. J. Respir. Cell Mol. Biol.* 41:722-730 (2009), which is hereby incorporated by reference in its entirety).

Seahorse bioassay: Extracellular acidification rates of human lung fibroblasts treated with TGF-b and/or gossypol were measured using The Seahorse XF96 system (Seahorse Bioscience, North Billerica, Mass.) according to the manufacturer's protocol. Fibroblasts were cultured with and without TGF-b for 72 hours to allow for the induction of myofibroblast differentiation. The differentiated fibroblasts were then transferred to XF96 cell culture plates and incubated a further 24 hours with TGF-b and/or gossypol, followed by determination of the extracellular acidification rate.

siRNA transfection: LDH5 siRNA (ON-TARGET SMART-pool, Thermo Scientific, which is a pool of four siRNA molecules specific for LDH5) was transfected using Simporter transfection reagent (Millipore, Temecula, Calif.). A non-specific scrambled siRNA was used as a control. Protein knockdown was confirmed by Western blot.

Statistical analyses: All data are expressed as means+/- SD. A Student's unpaired t-test and one way ANOVA with Tukey post-test comparisons were used to establish statistical significance using Graph Pad Prism software (version 5.04). Results were considered significant if $p<0.05$.

Example 1

Gossypol Inhibits TGF-β Induced Myofibroblast Differentiation in Healthy and Fibrotic Primary Human Lung Fibroblasts in a Dose Dependent Manner Myofibroblasts are one of the primary cell types responsible for the accumulation of extracellular matrix in fibrosing diseases, and targeting myofibroblast differentiation is an important therapeutic strategy for the treatment of pulmonary fibrosis. TGF-β has been shown to be an important inducer of myofibroblast differentiation. Applicants previously demonstrated that LDH and its metabolic product lactic acid are important mediators of myofibroblast differentiation, via acid-induced activation of latent TGF-β. As described herein, applicants investigated whether pharmacologic inhibition of LDH activity can prevent TGF-β induced myofibroblast differentiation.

Primary human lung fibroblasts were cultured with and without 1 ng/mL TGF-β and/or 1, 5, or 10 mM gossypol for 72 hours. Markers of myofibroblast differentiation, including expression of αSMA and calponin, were determined by WB. Gossypol inhibited both αSMA and calponin expression in a dose dependent manner (FIGS. 1A-1D). This finding was confirmed in two additional strains of healthy primary human lung fibroblasts.

Figure 2A:
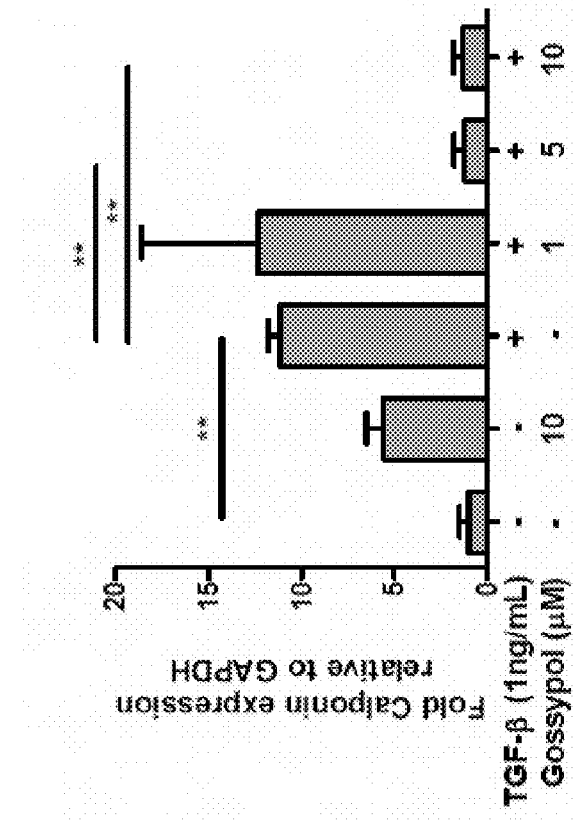
FIGS. 2A-2D show that gossypol inhibits TGF-β induced myofibroblast differentiation in fibroblasts obtained from donors with IPF. Normal primary human lung fibroblasts were cultured with and without 1 ng/mL TGF-β and/or 1, 5, or 10 mM gossypol for 72 hours. WB analysis of protein lysates was performed for markers of myofibroblast differentiation, αSMA (FIGS. 2A-2B) and calponin (FIGS. 2C-2D). Densitometry for n=3 replicates per condition, and representative WB images are shown. (Mean±SD, *=p<0.001, =p<0.01 by ANOVA compared to untreated cells). Three strains of primary IPF lung fibroblasts were tested, results from one representative strain are shown.
Figure 2B:
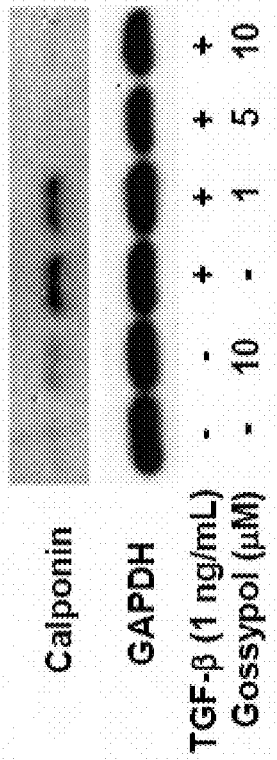
Figure 2C:
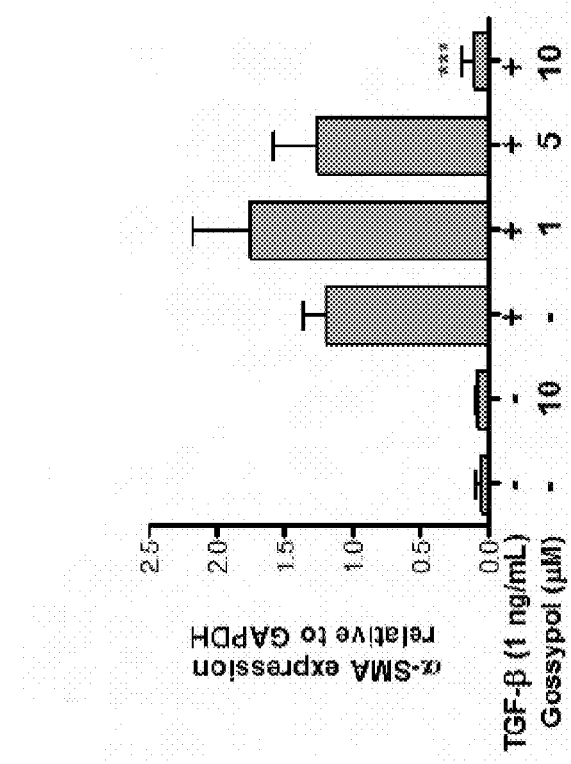
Figure 2D:
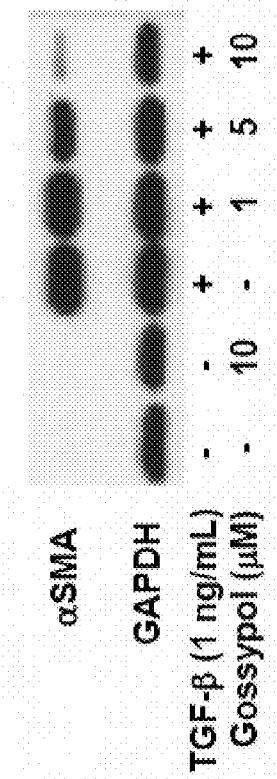

Immunofluorescent staining for αSMA demonstrated increased expression of actin filaments in fibroblasts treated with TGF-β. This change in morphology was prevented by gossypol (FIG. 1E). The efficacy of gossypol was next tested in primary human lung fibroblasts isolated from donors with pulmonary fibrosis. αSMA and calponin expression were determined by Western blot. Gossypol also inhibited αSMA (FIGS. 2A-2B) and calponin (FIGS. 2C-2D) expression in fibrotic primary human lung fibroblasts in a dose dependent manner. This finding was confirmed in two additional strains of fibrotic primary human lung fibroblasts.

Example 2

Gossypol Inhibits TGF-β Induced ECM Generation

Primary human lung fibroblasts were cultured with and without 1 ng/mL TGF-β and/or 1, 5, or 10 mM gossypol for 24 hours. Col1A1 and Col3A1 mRNA expression was determined by qRT-PCR and fibronectin expression was determined by WB. gossypol inhibited both Col1A1 and Col3A1 mRNA expression (FIGS. 3A-3B) and fibronectin expression (FIGS. 3C-3D) in a dose dependent manner.

Example 3

Figure 4A:
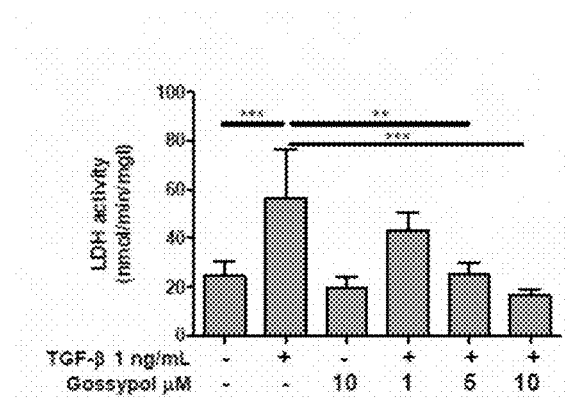
FIGS. 4A-4E show that gossypol inhibits LDH activity, extracellular acidification rates, the generation of extracellular lactic acid, and TGF-β bioactivity. Primary human lung fibroblasts were cultured with and without 1 ng/mL TGF-β for 72 hours at which time cells were lysed in a buffer that did not contain SDS. Gossypol was added to the lysates to achieve a final concentration of 1, 5, or 10 mM. LDH activity was assessed using a standardized spectrophotometric assay for the extinction of NADH (FIG. 4A) (Mean±SD for 3 replicates, *=$p<0.001$, =$p<0.01$ by ANOVA compared to untreated cells). For FIG. 4B, lung fibroblasts were cultured with and without 1 ng/mL TGF-β and/or 1, 5, or 10 mM gossypol for 72 hours. Lactic acid was measured in the supernatants using a commercially available assay (=$p<0.01$ by ANOVA compared to untreated cells). For FIG. 4C, fibroblasts were cultured with and without 1 ng/mL TGF-β and/or 1, 5, or 10 mM gossypol for 72 hours and subsequently transferred to a Seahorse bioassay plate for an additional 24 hours with fresh TGF-β and gossypol. The Seahorse XF96 analyzer was used to measure extracellular acidification rates, expressed as milli-pH units of change per minute. (*=$p<0.001$ by ANOVA compared to untreated cells, n=22 replicates each). For FIG. 4D, fibroblasts were cultured with and without 1 ng/mL TGF-β and/or 1, 5, or 10 mM gossypol for 72 hours. Cells were subsequently incubated with Alamar blue and intracellular reduction to the fluorescent product was assessed after four hours. Results expressed as percent of control, Mean±SD for n=4 wells per group, *=$p<0.001$, =$p<0.01$ by ANOVA. For FIG. 4E, active TGF-β was determined in conditioned medium from the fibroblast cultures from part C using the mink lung epithelial cell bioassay. Results are shown as percent incorporation normalized to control medium. In this assay, active TGF-β suppresses proliferation of the cells. (**=$p<0.01$ by ANOVA compared to untreated controls).
Figure 4B:
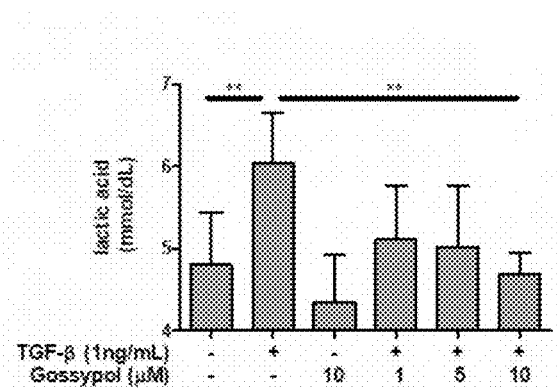
Figure 4C:
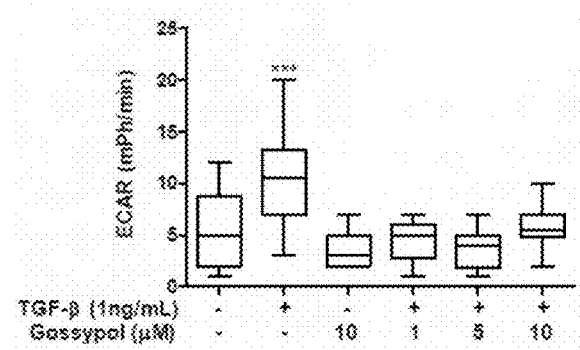
Figure 4D:
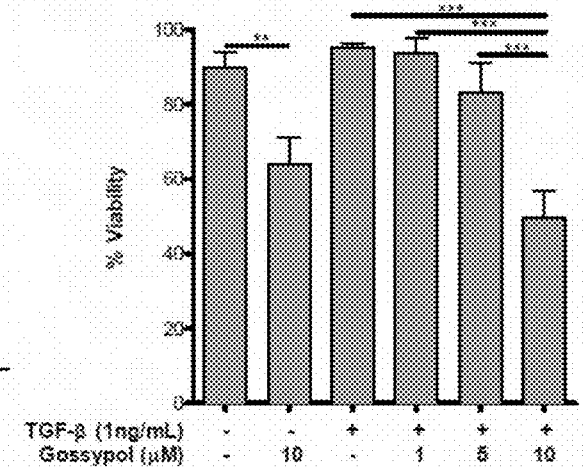

Gossypol Inhibits LDH Activity, Extracellular Acidification, Lactic Acid Production, and TGF-β Bioactivity in Primary Human Lung Fibroblasts Based on the foregoing results, it was believed that gossypol inhibits endogenous LDH activity, thus reducing lactate production and subsequent lactate-dependent activation of latent TGF-β in the medium. To investigate the mechanism of action of gossypol, fibroblasts were first treated with TGF-β for 72 hours. Next, protein lysates were harvested and incubated with increasing concentrations of gossypol for one hour. The LDH activity of each lysate was then determined with a standardized LDH kinetic activity assay. Gossypol inhibited LDH activity in protein lysates in a concentration dependent manner (FIG. 4A). Next, it was investigated whether gossypol could prevent the extracellular accumulation of lactate by treated fibroblasts. Lactic acid generation was inhibited by all doses of gossypol in both TGF-β treated and untreated fibroblasts (FIG. 4B). To confirm that gossypol inhibits extracellular accumulation of lactate, the rate of extracellular acidification was measured using the commercially available Seahorse Bioassay. TGF-β alone significantly increased the extracellular acidification rate in the fibroblasts, expressed as milli-pH units of change per minute (FIG. 4C). Gossypol significantly inhibited TGF-β stimulated extracellular acidification (FIG. 4C). To determine whether the effects of gossypol were dependent on toxic effects on the cells, the Alamar blue assay was utilized. 1 mM and 5 mM gossypol had no significant effect on Alamar blue reduction. Cells treated with 10 mM gossypol demonstrated a 50% decrease in Alamar blue reduction, indicating a reduction in cell viability or in mitochondrial activity at the highest dose tested (FIG. 4D).

Figure 4E:
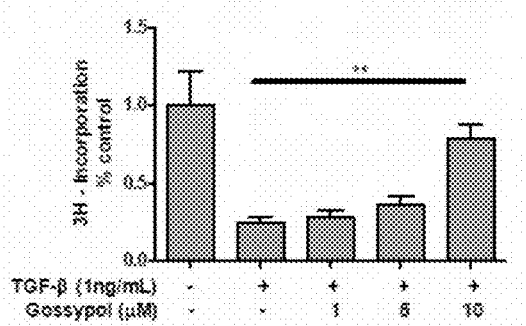

Finally, it was confirmed that reducing extracellular lactate production inhibited the activation of latent TGF-β in culture medium. Lung fibroblasts were treated for 72 hours with 1 ng/mL TGF-β and/or 1, 5, or 10 mM gossypol, and the conditioned medium was added to mink lung cells in standardized mink lung epithelial cell bioassay. In this assay, active TGF-β suppresses proliferation of the mink lung cells. Conditioned medium from gossypol-treated fibroblasts had less of a suppressing effect, demonstrating that gossypol-conditioned medium had less active TGF-β and confirming that gossypol inhibited the activation of latent TGF-β in the fibroblast cultures (FIG. 4E).

Example 4

Genetic Knock Down of LDH Enhances the Ability of Gossypol to Inhibit TGF-β Induced Myofibroblast Differentiation Applicants previously reported that genetic knockdown of LDH expression inhibited TGF-β stimulated myofibroblast differentiation. The efficacy of gossypol as a pharmaceutical approach was compared to the genetic knockdown approach. Primary lung fibroblasts were transfected with an LDH siRNA or control (scrambled) siRNA, followed by treatment with TGF-β and gossypol as indicated.

Figure 5A:
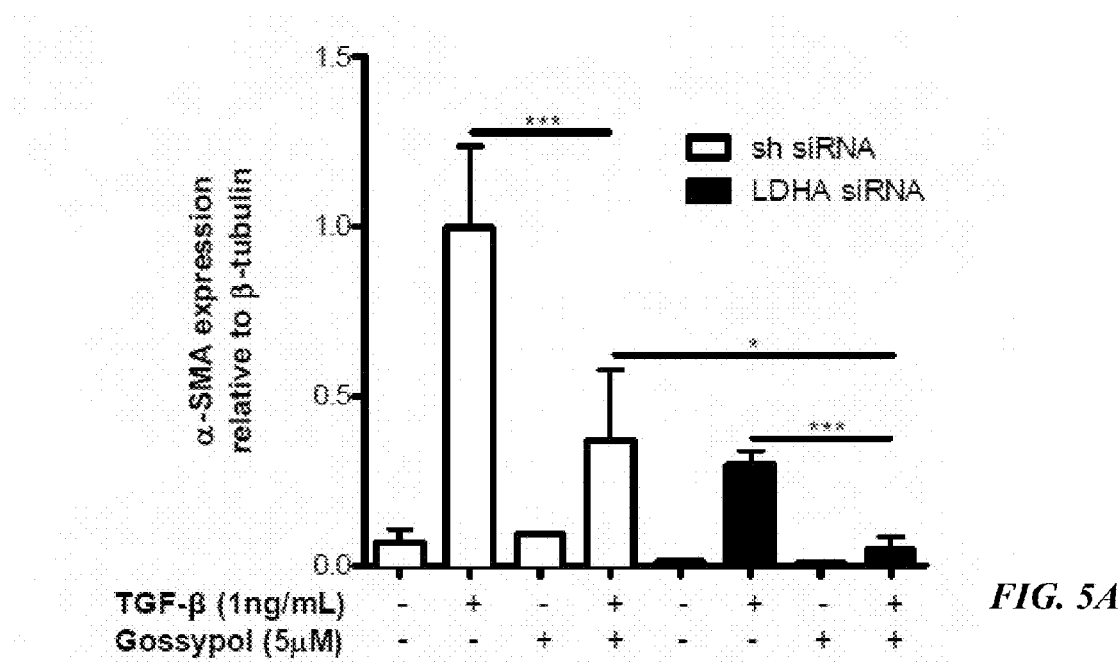
FIGS. 5A-5C show that gossypol is more effective at inhibiting myofibroblast differentiation when there is concurrent genetic inhibition of LDH.
Figure 5B:
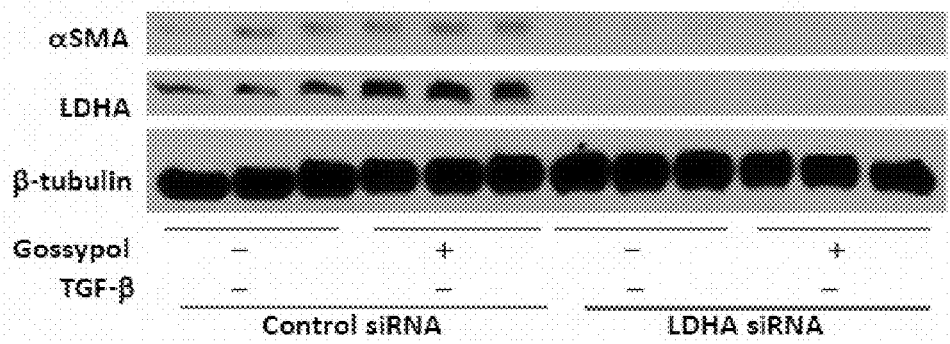
Figure 5C:
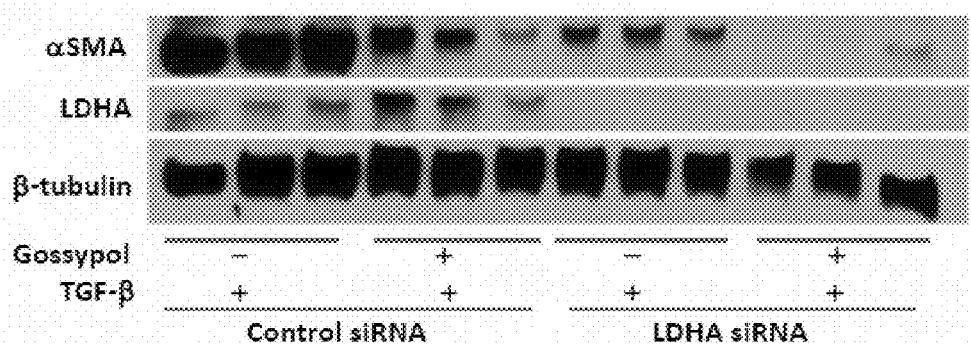

Gossypol alone significantly inhibited TGF-β-stimulated myofibroblast differentiation, with similar efficacy to LDH siRNA alone (FIGS. 5A and 5C). Interestingly, gossypol also reduced background levels of αSMA expression in cells without TGF-β stimulation (FIG. 5B), indicating that even under unstimulated conditions, there is some basal level of TGF-β activation driven by lactate. The combination of LDH knockdown and gossypol together completely inhibited TGF-β driven myofibroblast differentiation (FIG. 5C).

Discussion of Examples 1-4

Based on the foregoing Examples, it is believed that TGF-β and LDH act together to create a pro-fibrotic feed-forward loop in pulmonary fibrosis and possibly other fibrotic conditions. Increased expression of LDH results in the release of lactic acid into the extracellular matrix and activation of latent TGF-β. TGF-β, in addition to promoting myofibroblast differentiation directly, also upregulates expression of LDH and production of lactic acid Inhibition of LDH activity, therefore, should interrupt this cycle by reducing activation of latent TGF-β, and consequently downregulating pro-fibrotic effector functions including myofibroblast differentiation and ECM production. Examples 1-4 above demonstrate that gossypol, a pharmacologic inhibitor of lactate dehydrogenase, does indeed inhibit TGF-β induced myofibroblast differentiation with great efficacy. Gossypol inhibits upregulation of αSMA and calponin, makers of myofibroblast differentiation, in normal primary human lung fibroblasts (FIGS. 1A-E), as well as in fibroblasts obtained from fibrotic lung tissue (FIGS. 2A-D). In addition, gossypol also inhibits the generation of extracellular matrix components such as Collagen 1, Collagen 3 and Fibronectin (FIGS. 3A-D). Applicants confirmed that the primary mechanism by which gossypol inhibits myofibroblast differentiation is by inhibiting acid-dependent activation of latent TGF-β.

Examples 1-4 above also demonstrate that gossypol inhibits myofibroblast differentiation with similar efficacy to genetic inhibition of LDH expression (FIGS. 5A-C). This is significant, and not at all expected. Indeed, genetic inhibition of gene expression, while effective in vitro, presents significant challenges in a clinical setting. LDH is a promising therapeutic target for a variety of malignancies (Ready et al., "Double-Blind, Placebo-Controlled, Randomized Phase 2 Study of the Proapoptotic Agent AT-101 Plus Docetaxel, in Second-Line Non-Small Cell Lung Cancer," *J. Thorac. Oncol.* 6:781-785 (2011); Schelman et al., "A Phase I Study of AT-101 with Cisplatin and Etoposide in Patients with Advanced Solid Tumors with an Expanded Cohort in Extensive-Stage Small Cell Lung Cancer," *Invest. New Drugs* 32:295-302 (2014); Sonpavde et al., "Randomized Phase II Trial of Docetaxel Plus Prednisone in Combination with Placebo or AT-101, an Oral Small Molecule Bcl-2 Family Antagonist, as First-Line Therapy for Metastatic Castration-Resistant Prostate Cancer," *Ann. Oncol.* 23:1803-1808 (2012); Liu et al., "An Open-Label, Multicenter, Phase I/II Study of Single-Agent AT-101 in Men with Castrate-Resistant Prostate Cancer," *Clin. Cancer Res.* 15:3172-3176 (2009); and Van Poznak et al., "Oral gossypol in the Treatment of Patients with Refractory Metastatic Breast Cancer: A Phase I/II Clinical Trial," *Breast Cancer Res. Treat.*

66:239-248 (2001), which are hereby incorporated by reference in their entirety), and systemic inhibition of LDH is clinically feasible and can be well tolerated. Additionally, anti-LDH pharmacotherapies are in development along with strategies to more precisely target specific organs and cell types. It is interesting to note that gossypol was effective in inhibiting myofibroblast differentiation even in LDHA knockdown cells (FIG. 5C). There are several possible explanations for this effect, the simplest of which is that complete knockdown was not achieved. However, it should also be remembered that lactate dehydrogenase encompasses 5 tetrameric isozymes made up of varying ratios of the LDH-M and LDH-H subunit peptides. While RNA silencing of the LDHA gene reduces the expression of the M subunit of LDH causing a reduction in the protein levels of the LDH2-5 isoenzymes ($H_3M_1$, $H_2M_2$, $H_1M_3$, and $M_4$, respectively), it will not affect expression of LDH1 ($H_4$). Although the LDH5 isoenzyme, $M_4$, is reported to be the primary generator of lactate, a contribution from LDH1 and the LDHB gene cannot be ruled out. Thus, pharmacologic inhibition of LDH activity is likely more promising than knockdown of specific subunits.

Also, it is worth noting that lactic acid will not induce the myofibroblast differentiation without a source of latent TGF-β (such as fetal bovine serum) (Kottmann et al., "Lactic Acid is Elevated in Idiopathic Pulmonary Fibrosis and Induces Myofibroblast Differentiation Via pH-Dependent Activation of Transforming Growth Factor-Beta," *Am. J. Respir. Crit. Care Med.* 186:740-751 (2012), which is hereby incorporated by reference in its entirety). This indicates that activation of latent TGF-β is an integral and necessary step in myofibroblast differentiation. As it is well known that the extracellular matrix in human lung tissue contains large stores of latent TGF-β, this supports the belief that inhibition of LDH activity should be a surprisingly potent clinical strategy.

Gossypol is reported to target other cellular processes in addition to LDH activity. For example, in cancer cells it can inhibit cell cycle progression and promote apoptosis (Lin et al., "Induction of Apoptosis and Antitumor Effects of a Small Molecule Inhibitor of Bcl-2 and Bcl-xl, gossypol Acetate, in Multiple Myeloma In vitro and In vivo," *Oncol. Rep.* 30:731-738 (2013); Sun et al., "Apogossypol Inhibits Cell Growth by Inducing Cell Cycle Arrest in U937 Cells," *Oncol. Rep.* 22:193-198 (2009); Li et al., "Liposomes Containing (−)-Gossypol-Enriched Cottonseed Oil Suppress Bcl-2 and Bcl-xL Expression in Breast Cancer Cells," *Pharm. Res.* 28:3256-3264 (2011); Deng et al., "Gossypol Acetic Acid Induces Apoptosis in RAW264.7 Cells Via a Caspase-Dependent Mitochondrial Signaling Pathway," *J. Vet. Sci.* 14:281-289 (2013); and Hsiao et al., "Involvement of Smac, p53, and Caspase Pathways in Induction of Apoptosis by Gossypol in Human Retinoblastoma Cells," *Mol. Vis.* 18:2033-2042 (2012), which are hereby incorporated by reference in their entirety). Although Examples 1-4 have focused on inhibition of LDH activity as a pathway to blocking TGF-β activity, these other activities could potentially be important in treating fibrosis. It is well-known that myofibroblasts in fibrosing diseases are resistant to apoptosis, a mechanism thought to be important in dampening the wound healing response and promoting tissue remodeling (Ramos et al., "Fibroblasts from Idiopathic Pulmonary Fibrosis and Normal Lungs Differ in Growth Rate, Apoptosis, and Tissue Inhibitor of Metalloproteinases Expression," *Am. J. Respir. Cell Mol. Biol.* 24:591-598 (2001) and Zhang et al., "Inhibition of Myofibroblast Apoptosis by Transforming Growth Factor Beta(1)," *Am. J. Respir. Cell Mol. Biol.* 21:658-665 (1999), which are hereby incorporated by reference in their entirety). Proliferation of fibroblasts and myofibroblasts is a significant factor in the pathogenesis of fibrosis (Kendall et al., "Fibroblasts in Fibrosis: Novel Roles and Mediators," *Front Pharmacol.* 5:123 (2014) and Wynn, "Integrating Mechanisms of Pulmonary Fibrosis," *J. Exp. Med.* 208:1339-1350 (2011), which are hereby incorporated by reference in their entirety), in addition to production of ECM. Although gossypol was a potent inhibitor of myofibroblast differentiation and function at concentrations that did not reduce cell viability, it is noteworthy that the anti-proliferative and potential pro-apoptotic properties of gossypol could also be important in developing gossypol as an IPF therapy.

Despite the recent discovery of two new medications (Pirfenidone and Nintedanib), pulmonary fibrosis remains a progressive disease (Raghu et al., "Nintedanib and Pirfenidone. New Antifibrotic Treatments Indicated for Idiopathic Pulmonary Fibrosis Offer Hopes and Raises Questions," *Am. J. Respir. Crit. Care Med.* 191:252-254 (2015); King et al., "A Phase 3 Trial of Pirfenidone in Patients with Idiopathic Pulmonary Fibrosis," *N. Engl. J. Med.* 370:2083-2092 (2014); and Richeldi et al., "Efficacy and Safety of Nintedanib in Idiopathic Pulmonary Fibrosis," *N. Engl. J. Med.* 370:2071-2082 (2014), which are hereby incorporated by reference in their entirety). The data found in Examples 1-4 support the role of LDH inhibition in the prevention of TGF-β induced myofibroblast differentiation and potentially in the treatment of pulmonary fibrosis. Applicants acknowledge that gossypol likely has other potential inhibitory properties that may be involved in the prevention of myofibroblast differentiation, but the presented data strongly support the importance of the role of LDH inhibition in its mechanism of action.

Example 5

Gossypol Inhibits Bleomycin-Induced Pro-Fibrotic Gene Expression and Pulmonary Fibrosis In Vivo Applicants have previously demonstrated the importance of excess LDH and lactic acid in driving myofibroblast differentiation (Kottmann et al., "Lactic Acid is Elevated in Idiopathic Pulmonary Fibrosis and Induces Myofibroblast Differentiation Via pH-Dependent Activation of Transforming Growth Factor-Beta," *Am. J. Respir. Crit. Care Med.* 186:740-751 (2012), which is hereby incorporated by reference in its entirety). It is believed, based on the preceding Examples, that LDH5, lactic acid and latent TGF-β together contribute to a feed-forward pro-fibrotic loop in lung tissue and contribute to the development and/or progression of pulmonary fibrosis. As demonstrated in the preceding Examples, pharmacologic inhibition of LDH represents an important new therapy for pulmonary fibrosis.

To test this therapy in vivo, a bleomycin-induced pulmonary fibrosis model was selected to assess the efficacy of gossypol. Bleomycin induces the expression of LDH5 in lung tissue. Briefly, 1.5 units/kg of bleomycin or PBS control was administered to C57BL6 mice (n=6 in each group) via oropharyngeal aspiration. Mice were concomitantly treated with PBS (control), or 10 mg/kg or 25 mg/kg of the LDH inhibitor gossypol for 7 days via intra-peritoneal injection ("i.p."). Mice were weighed daily and sacrificed on day 7. BALF was analyzed for cell count and differential, and lung tissue was analyzed for expression of Col1A1 mRNA and FN mRNA.

Figure 6A:
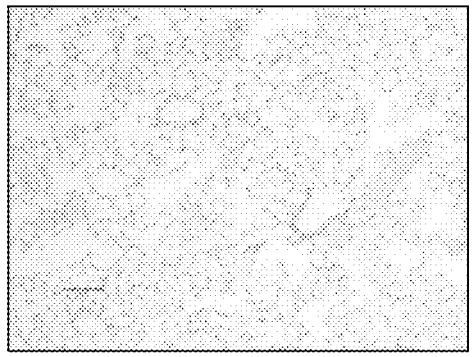
FIGS. 6A-6E show that bleomycin induces the expression of LDH5 in lung tissue. C57BL6 mice were administered bleomycin via oropharyngeal aspiration and sacrificed on day 21. Lung tissue sections were stained for LDH5. There was minimal expression of LDH5 in mice treated with PBS (FIG. 6A). Mice treated with bleomycin had increased expression of LDH5 that localized to the interstitium (FIG. 6B), the interstitial cells (FIG. 6C), and small airway epithelium (FIG. 6D) but not the larger airway epithelium (FIG. 6E).
Figure 6B:
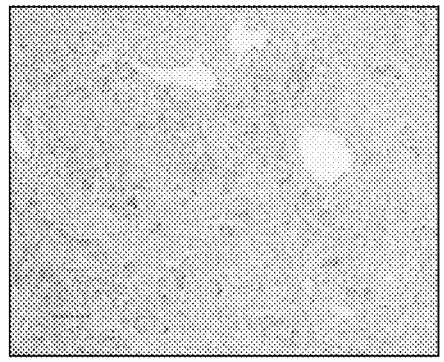
Figure 6C:
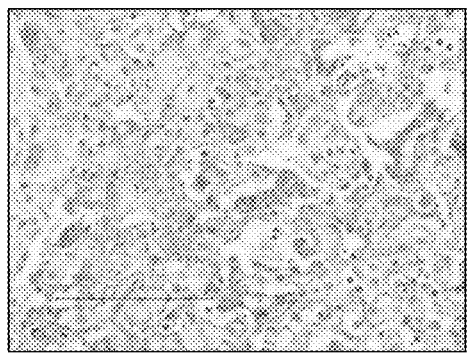
Figure 6D:
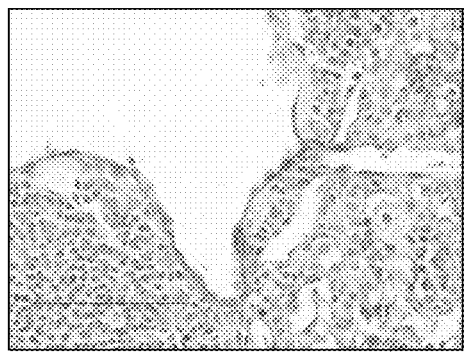
Figure 6E:
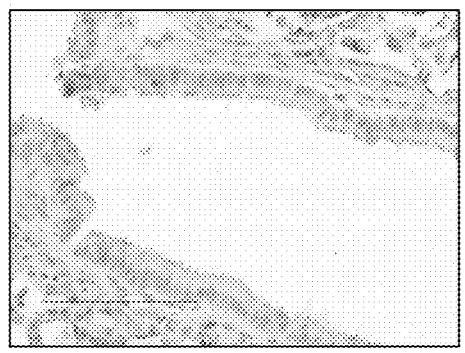

Lung tissue sections of mice administered bleomycin were stained for LDH5. Mice treated with bleomycin had increased expression of LDH5 that localized to the interstitium (FIG. 6B), the interstitial cells (FIG. 6D), and small airway epithelium (FIG. 6D) but not to the larger airway epithelium (FIG. 6E) as compared to lung tissue sections of control mice treated with PBS (FIG. 6A).

Figures 7A, 7B:
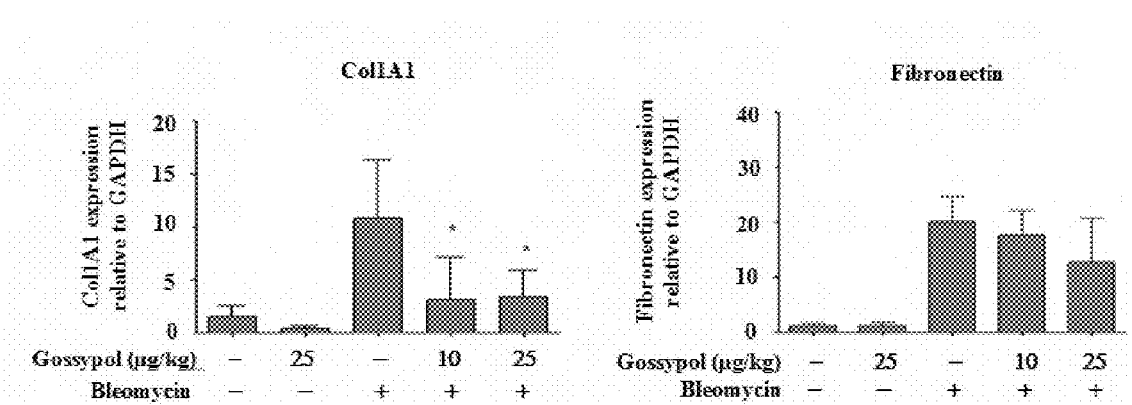
FIGS. 7A-7B show gossypol inhibition of bleomycin-induced pro-fibrotic gene expression. C57BL6 mice were administered bleomycin via oropharyngeal aspiration. Mice were subsequently dosed daily with either PBS or gossypol (10 mg/kg or 25 mg/kg) via intra-peritoneal injection. Mice were sacrificed on day 7 and RNA was extracted from whole lung tissue. qRT-PCR was used to analyze Col1A1 and Fibronectin mRNA expression (n=6 for each group, * $p<0.01$).

It was also assessed whether gossypol can inhibit bleomycin-induced pro-fibrotic gene expression in vivo. RNA extracted from whole lung tissue of C57BL6 mice administered bleomycin and treated with varying doses of gossypol (0, 10, or 25 µg/kg) was analyzed by qRT-PCR for Col1A1 and FN mRNA expression (FIGS. 7A-7B) and compared to controls. Gossypol significantly reduced Col1A1 mRNA expression (FIG. 7A). A trend toward a reduction in bleomycin-induced FN mRNA expression in mice treated with gossypol was observed (FIG. 7B).

Figures 8A, 8B:
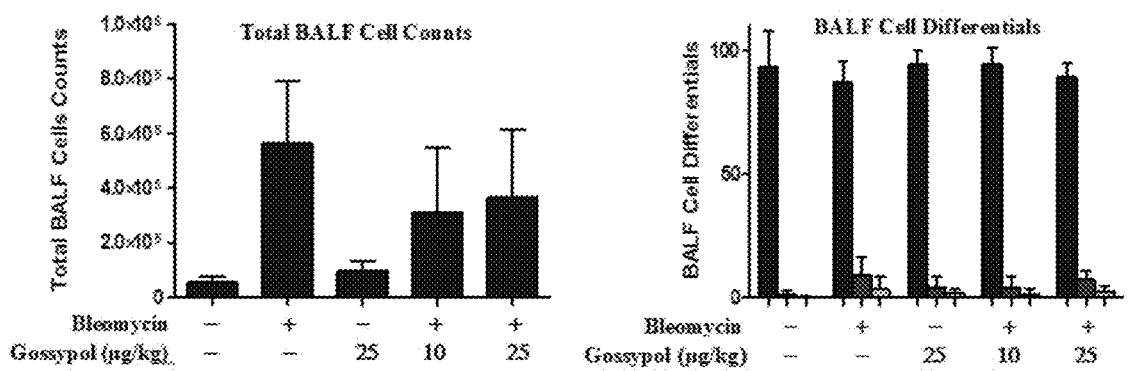
FIGS. 8A-8B show that low dose gossypol reduces bleomycin-induced lung inflammation and affects differential cell counts. C57BL6 mice were administered bleomycin via oropharyngeal aspiration and dosed daily with either PBS or gossypol (10 mg/kg or 25 mg/kg) via intra-peritoneal injection. Mice were sacrificed on day 7 and BALF was collected. Total BALF cell counts and cell differentials were determined (n=6 for each group). Neither dose of gossypol significantly reduced bleomycin-induced inflammatory cells in the BALF (FIG. 8A) nor did gossypol significantly alter the differential cell counts (FIG. 8B).

To test whether low dose gossypol reduces bleomycin-induced lung inflammation or affects cell differentials, C57BL6 mice were administered bleomycin via oropharyngeal aspiration and dosed daily with either PBS or gossypol (10 mg/kg or 25 mg/kg) via intra-peritoneal injection. Mice were sacrificed on day 7 and BALF was collected. Neither dose of gossypol significantly reduced bleomycin-induced inflammatory cells in the BALF (FIG. 8A) nor did gossypol significantly alter the differential cell counts (FIG. 8B).

Figure 9A:
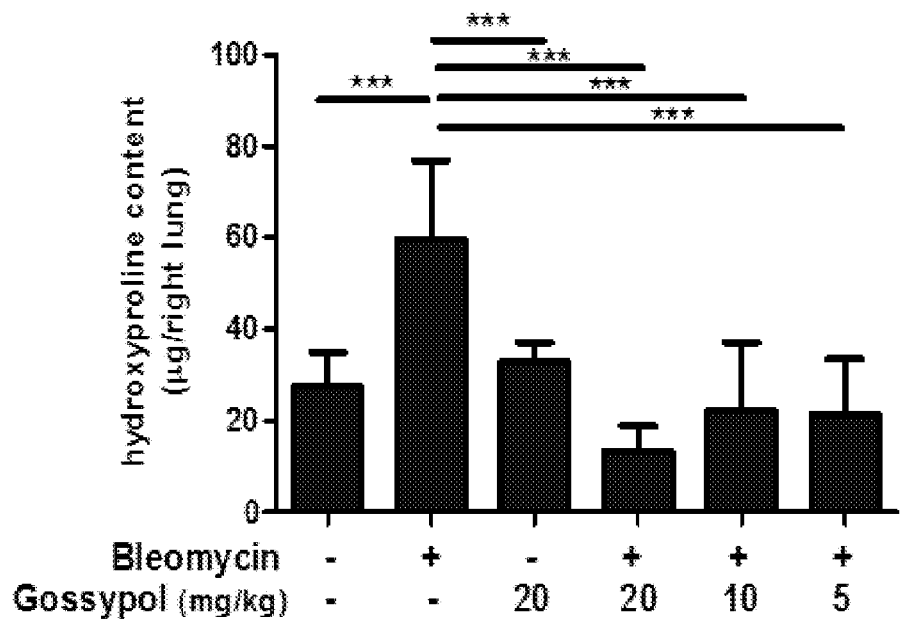
FIGS. 9A-9B show gossypol inhibition of pulmonary fibrosis in vivo. C57BL6 mice were administered bleomycin via oropharyngeal aspiration and dosed daily with either PBS or gossypol (5, 10, or 25 mg/kg via subcutaneous injection). Mice were sacrificed on day 21 and whole lung tissue was processed for hydroxyproline content and histology. Gossypol significantly inhibited bleomycin-induced hydroxyproline expression at all of the doses tested (FIG. 9A; n=10 ***$p<0.001$). Trichrome stains demonstrate a marked reduction in pulmonary fibrosis and collagen deposition (FIG. 9B).
Figure 9B:
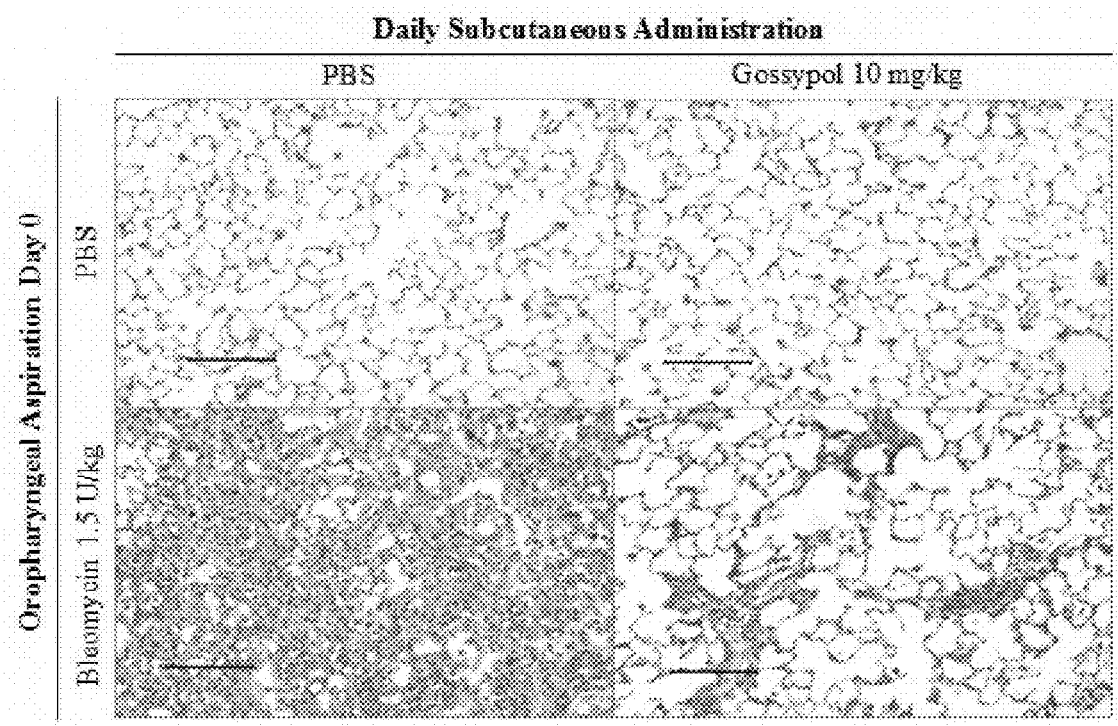

Next, gossypol inhibition of pulmonary fibrosis was examined in vivo. Whole lung tissue from C57BL6 mice administered bleomycin and dosed daily with either PBS or gossypol (5, 10, or 25 mg/kg via subcutaneous injection) was evaluated. Gossypol significantly inhibited bleomycin-induced hydroxyproline expression at all of the doses tested (FIG. 9A). Trichrome stains demonstrate a marked reduction in pulmonary fibrosis and collagen deposition (FIG. 9B).

LDH5 is over-expressed in the lung tissue of patients with pulmonary fibrosis (Kottmann et al., "Lactic Acid is Elevated in Idiopathic Pulmonary Fibrosis and Induces Myofibroblast Differentiation Via pH-Dependent Activation of Transforming Growth Factor-Beta," *Am. J. Respir. Crit. Care Med.* 186:740-751 (2012), which is hereby incorporated by reference in its entirety). Bleomycin induces LDH5 expression in mouse lung tissue. Low dose gossypol inhibits bleomycin-induced Col1A1 expression, shows a dose dependent trend in the inhibition of bleomycin-induced fibronectin expression, and it also inhibits bleomycin-induced hydroxyproline expression and pulmonary fibrosis in vivo.

Materials and Methods for Examples 6-11

Human Cell Culture and Tissue Samples: Primary human lung fibroblast strains were derived from tissue explants as previously described (Ferguson et al., "Electrophilic Peroxisome Proliferator-Activated Receptor-Gamma Ligands Have Potent Antifibrotic Effects in Human Lung Fibroblasts," *Am. J. Respir. Cell Mol. Biol.* 41:722-730 (2009), which is hereby incorporated by reference in its entirety). All donors gave informed written consent. Tissue sections from patients with radiation induced lung fibrosis or control (non-fibrotic) tissue sections were obtained from the Department of Pathology at the University of Rochester and were de-identified. All human subjects research was performed under the supervision of the University of Rochester Research Subjects Review Board (RSRB).

Cell Culture and Irradiations: Fibroblasts were cultured in Eagle's minimum essential media (Life Technologies, Gaithersburg, Md.) supplemented with 10% FBS (Sigma Aldrich, St. Louis, Mo.), 2 mM L-Glutamine, antibiotic and antimycotic (Gibco, Carlsbad, Calif.) at 37° C. with 7% $CO_2$. Cells were irradiated with a $^{137}Cs$ γ-ray source at approximately 2.70 cGy/min dose rate at indicated doses. Human recombinant TGF-β1 (R&D systems, Minneapolis, Minn.) was used at 1 ng/ml. LDHA was genetically inhibited using Smart Pool ONTARGET siRNA or Smart Pool Non-targeting Control Pool (Thermo Scientific, Waltham, Mass.) and siImporter transfection reagent (Upstate Cell Signaling Solutions, Charlottesville, Va.) according to the manufacturer's specifications. Cells were transfected 18 hours prior to irradiation. TGF-β1 receptor 1 was inhibited using SB431542 (Sigma Aldrich) at 2.5 µM starting 1 hour prior to irradiations. Cell viability was measured using Alamar Blue reagent (Invitrogen, Carlsbad, Calif.) according to the manufacturer's specifications. LDHA was pharmacologically inhibited with Gossypol (Sigma Aldrich) at indicated doses starting 1 hour prior to irradiations.

TGF β Bioassay: A TGF-β bioassay was performed as previously described (Kottmann et al., "Lactic Acid is Elevated in Idiopathic Pulmonary Fibrosis and Induces Myofibroblast Differentiation Via pH-Dependent Activation of Transforming Growth Factor-Beta," *Am. J. Respir. Crit. Care Med.* 186:740-751 (2012), which is hereby incorporated by reference in its entirety). Briefly, Mv1Lu mink lung epithelial cells were cultured with conditioned media from irradiated human lung fibroblasts for 24 hours before proliferation rates were measured using a 3H labelled thymidine incorporation assay. The inverse of proliferation rates are expressed as a fold change from 0 Gy controls.

Western Blotting: Cell lysates were run on SDS-PAGE under reducing conditions and probed for expression of α-SMA (Sigma Aldrich), LDHA (Abcam, Cambridge, Mass.). Glyceraldehyde 3-phosphate dehydrogenase (Abcam) was used as a loading control. Densitometry was performed as previously described (Ferguson et al., "Electrophilic Peroxisome Proliferator-Activated Receptor-Gamma Ligands Have Potent Antifibrotic Effects in Human Lung Fibroblasts," *Am. J. Respir. Cell Mol. Biol.* 41:722-730 (2009), which is hereby incorporated by reference in its entirety).

Immunohistochemistry: Paraffin embedded lung tissue sections from de-identified patients with radiation-induced fibrosis, or from C57BL/6 mice exposed to 5 Gy total body plus 10 Gy thoracic radiation as previously described (Manning et al., "Lung Irradiation Increases Mortality After Influenza A Virus Challenge Occurring Late After Exposure," *Internat'l J Radiation Oncol., Biol., Phys.* 86:128-135 (2013), which is hereby incorporated by reference in its entirety) were stained for α-SMA (Sigma Aldrich) and LDHA (Abcam) as previously described (Kottmann et al., "Lactic Acid is Elevated in Idiopathic Pulmonary Fibrosis and Induces Myofibroblast Differentiation Via pH-Dependent Activation of Transforming Growth Factor-Beta," *Am. J. Respir. Crit. Care Med.* 186:740-751 (2012), which is hereby incorporated by reference in its entirety).

Immunofluorescence: Primary human lung fibroblasts were irradiated in T-25 flasks, then trypsinized the next day and sub-cultured for 48 hours in glass chamber slides for immunofluorescence staining Cells were then fixed in 4% paraformaldehyde and stained with an antibody to α-SMA (Sigma Aldrich) followed by an anti-mouse AlexaFluor 568 (Invitrogen). Slides were mounted with Prolong Gold (Invitrogen) supplemented with DAPI to visualize nuclei and imaged using a Zeiss Axio Imager Z.I Microscope.

Quantitative Real-Time Polymerase Chain Reaction: RNA was isolated from primary human lung fibroblast and mouse lungs as previously described (Ferguson et al., "Electrophilic Peroxisome Proliferator-Activated Receptor- Gamma Ligands Have Potent Antifibrotic Effects in Human Lung Fibroblasts," *Am. J. Respir. Cell Mol. Biol.* 41:722-730 (2009), which is hereby incorporated by reference in its entirety). Reverse transcription was performed using iScript cDNA Synthesis Kit (Bio-Rad, Hercules, Calif.). Real-time polymerase chain reaction was performed using SsoAdvanced SYBR Green (Bio-Rad). The following primer sequences were used: human 18S:

```
Forward,
                                 (SEQ ID NO: 3)
GGTCGCTCGCTCCTCTCCCA;
and Reverse,
                                 (SEQ ID NO: 4)
AGGGGCTGACCGGGTTGGTT;

human Col1a1:
Forward,
                                 (SEQ ID NO: 5)
TTGAAGGAGGATGTTCCCATCT;
and Reverse,
                                 (SEQ ID NO: 6)
ACAGACACATATTTGGCATGGTT;

Col3a1:
Forward,
                                 (SEQ ID NO: 7)
TTGAAGGAGGATGTTCCCATCT;
and Reverse,
                                 (SEQ ID NO: 8)
ACAGACACATATTTGGCATGGTT;

mouse 18S:
Forward,
                                 (SEQ ID NO: 9)
GCTTGCTCGCGCTTCCTTACCT;
and Reverse,
                                 (SEQ ID NO: 10)
TCACTGTACCGGCCGTGCGTA;

mouse LDHA:
Forward,
                                 (SEQ ID NO: 11)
TGGCGACTCCAGTGTGCCTG;
and Reverse,
                                 (SEQ ID NO: 12)
AGGCACTGTCCACCACCTGCT.
```

Soluble Collagen Slot Blot: Soluble collagen was measured in cell supernatants as previously described (Lehmann et al., "The Aryl Hydrocarbon Receptor Ligand ITE Inhibits TGFbeta1-induced Human Myofibroblast Differentiation," *Am J Pathol* 178:1556-1567 (2011), which is hereby incorporated by reference in its entirety). Briefly, cell supernatants were applied to a PVDF membrane using a vacuum manifold (Schleicher and Schuell, Keene, N. H.) under non-denaturing conditions. Membranes were probed using an antibody to collagen 1 (Santa Cruz Biotechnology, Dallas, Tex.).

Seahorse Bioanalyzer Extracellular Acidification Rate (ECAR) Measurement: Primary human lung fibroblasts were irradiated in T-25 flasks, then trypsinized the next day and sub-cultured into XF96 well plates at 5,000 cells per well (Seahorse Bioscience, North Billerica, Mass.). The extracellular acidification rate (ECAR) was measured using a Seahorse Bioscience XF96 Flux Analyzer according to company specifications. Briefly, ECAR was measured every 5 minutes for 1 hour. Data was analyzed once cells equilibrated to calibration fluid and extracellular acidification rates reached a plateau (after about 20 minutes).

Lactate Measurements: Lactate levels were measured in cell supernatants using a Nova BioProfile Automated Analyzer (Nova Biomedical, Waltham, Mass.) according to company specifications. Lactate levels are expressed as fold change from 0 Gy controls.

Statistical Analysis: All data are expressed as mean±standard deviation. T-test and one-way analysis of variance (ANOVA) with Tukey post-test were used to establish statistical significance using Graph Pad Prism software (La Jolla, Calif.). Results were considered significant if the p-value was less than 0.05.

Example 6

LDHA Expression is Increased in Radiation-Induced Pulmonary Fibrosis

Figures 10A, 10B, 10C, 10D, 10E, 10F, 10G:
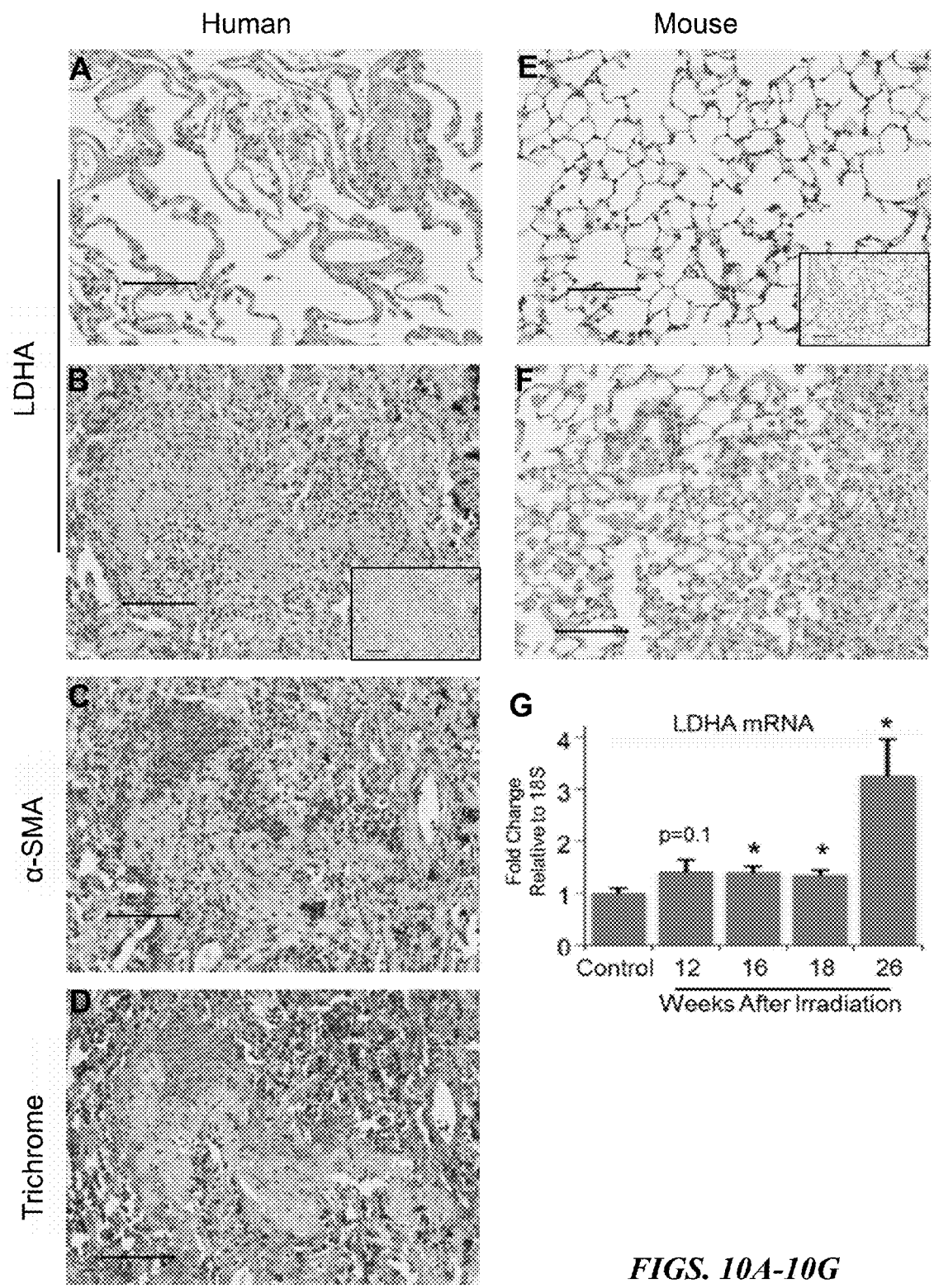
FIG. 10A-10G illustrate LDHA expression is increased in radiation-induced fibrotic lung tissue.

To investigate whether LDHA is increased in radiation-induced pulmonary fibrosis, immunohistochemical staining for LDHA and α-smooth muscle actin ("α-SMA") was performed on serial paraffin embedded tissue sections from patients with radiation-induced pulmonary fibrosis and non-irradiated controls. (FIGS. 10A-10C). Fibrotic lung tissue was also stained with Gomori's Trichrome to visualize collagen deposition (FIG. 10D). Lung tissue from patients with radiation-induced pulmonary fibrosis had increased cellular content in the interstitium compared to healthy lung tissue (FIGS. 10B-10C), with increased staining for α-SMA, a marker of myofibroblast differentiation. There was increased staining for LDHA (FIG. 10C) corresponding to areas of intense α-SMA expression (FIG. 10B-10C).

LDHA expression was also increased in the lung tissue in C57BL/6 mice 26 weeks after exposure to 5 Gy total-body plus 10 Gy thoracic irradiation (FIG. 10E-10F). Non-irradiated control mice showed some LDHA staining, which was primarily localized in the alveolar epithelium (FIG. 10E). However, mice exposed to radiation had increased cellular content in the interstitium and increased LDHA staining localized to the interstitium compared to non-irradiated controls. LDHA mRNA expression was measured with quantitative real-time PCR ("qRT-PCR") in total lung homogenates harvested between 12-26 weeks post radiation. Compared to non-irradiated control mice, mice exposed to radiation had increased LDHA mRNA levels starting at 16 weeks post-radiation (FIG. 10G). By 26 weeks, mice exposed to radiation had a 3-fold increase in LDHA mRNA levels compared to control mice (FIG. 10G).

Example 7

Ionizing Radiation Induces LDHA Expression and Lactate Production in Primary Human Lung Fibroblasts To investigate the mechanisms involved in radiation-induced pulmonary fibrosis, whether ionizing radiation induces the expression of LDHA in primary human lung fibroblast cultures was next determined. Lung fibroblasts were irradiated with 0, 3, 7, and 10 Gy of ionizing radiation and viability was assessed after 5 days using the Alamar Blue assay. Because 10 Gy resulted in a significant decrease in cell viability compared to 3 and 7 Gy (FIG. 11A), 3 and 7 Gy was used for the remaining experiments.

Ionizing radiation induced LDHA expression in primary human lung fibroblasts in a dose-dependent manner, with a greater than 5-fold induction at 7 Gy (FIGS. 11B-11C). Importantly, radiation exposure also significantly increased the rate at which irradiated fibroblasts released acid into the media (extracellular acidification rate, ECAR). At least some of this extracellular acid release was in the form of lactate, as cell supernatants from irradiated fibroblasts contained significantly higher levels of lactate (FIG. 11E).

Example 8

Ionizing Radiation Induces Myofibroblast Differentiation

Figure 12A:
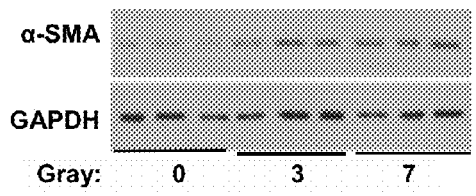
FIGS. 12A-12F illustrate that ionizing radiation induces myofibroblast differentiation. Primary lung fibroblasts were exposed to 0, 3 and 7Gy and cell lysates and supernatants were collected at 5 days post radiation.
Figure 12B:
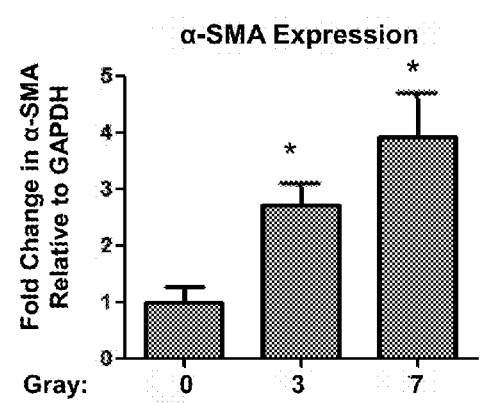
Figure 12C:
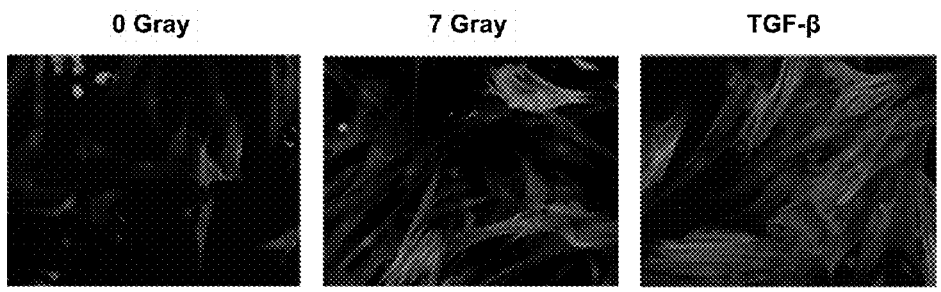
Figure 12D:
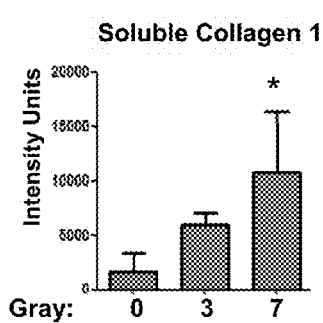
Figure 12E:
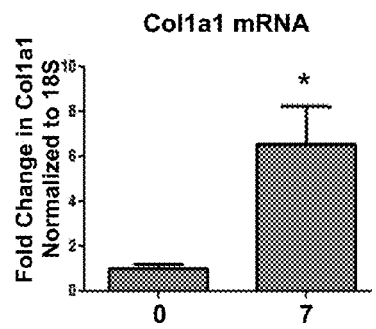
Figure 12F:
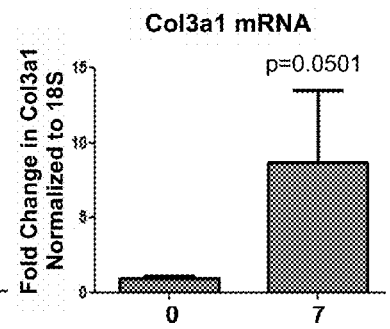

Irradiated lung tissue expresses high levels of α-SMA, a marker of myofibroblast differentiation (FIG. 10). To determine whether ionizing radiation induces myofibroblast differentiation, primary human lung fibroblasts were exposed to 3 and 7 Gy ionizing radiation and cultured for 5 days. Radiation induced α-SMA expression in a dose-dependent manner (FIG. 12A-12B). α-SMA was also analyzed using immunofluorescence staining 7 Gy radiation caused a significant increase in actin fiber staining following radiation in a similar manner to the induction of α-SMA by transforming growth factor beta ("TGF-β") (FIG. 12C). In addition, 7 Gy induced extracellular soluble collagen 1 protein (FIG. 12D) and in collagen 1 and 3 mRNA expression (FIG. 12E-12F).

Example 9

Ionizing Radiation Induces Activation of Latent TGF-β

Figure 13A:
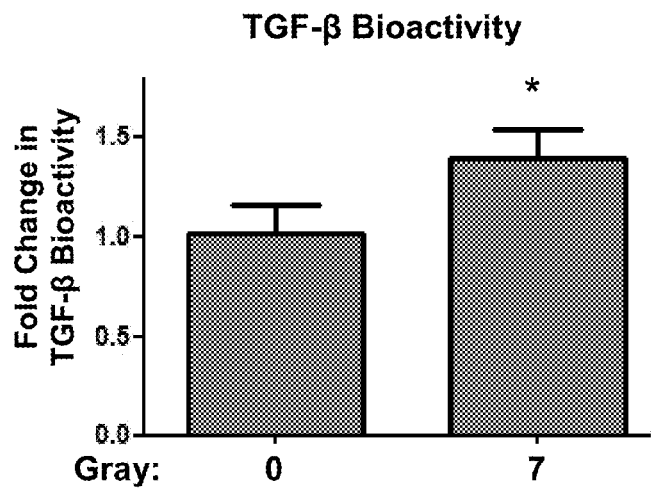
FIGS. 13A-13C illustrate that ionizing radiation activates latent TGF-β.
Figure 13B:
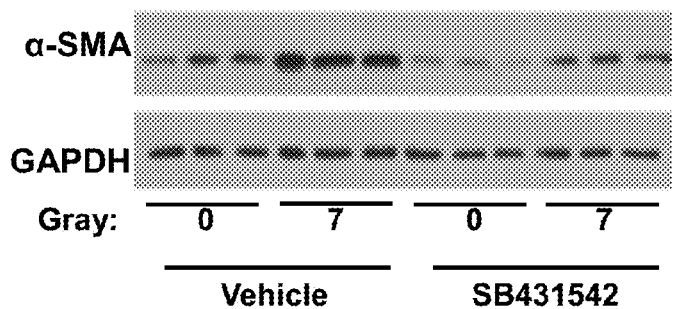
Figure 13C:
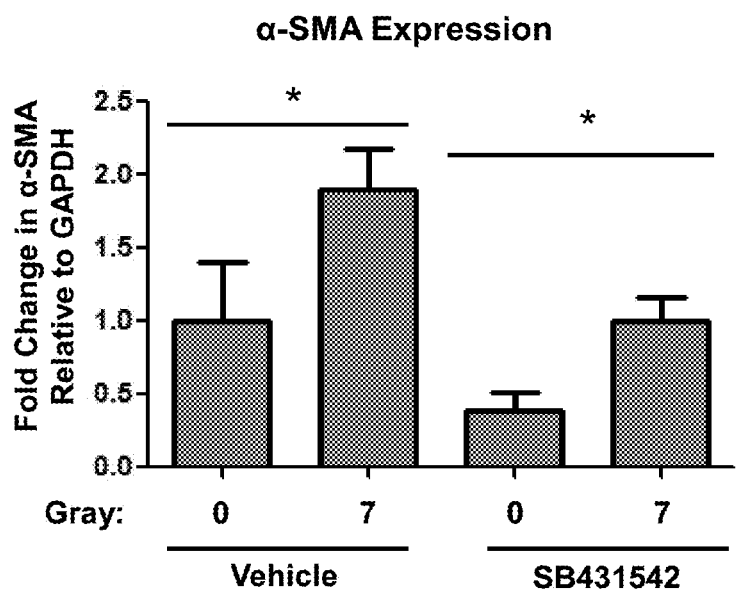

TGF-β has been reported to play an important role in radiation-induced tissue injury in multiple organs, including skin and lung. Furthermore, the prior Examples demonstrate that lactate can activate latent TGF-β in human lung fibroblast cultures. To test whether radiation leads to activation of latent TGF-β in human lung fibroblast cultures, a mink lung epithelial cell bioassay was performed on cell supernatants from control and irradiated cultures to determine levels of TGF-β bioactivity. 7 Gy radiation significantly increased TGF-β bioactivity in cell culture media from irradiated cells (FIG. 13A). To demonstrate that myofibroblast differentiation is driven by this activation of latent TGF-β, and not some other effect of ionizing radiation, fibroblasts were incubated with specific TGF-β receptor 1 inhibitor SB431542 (Inman et al., "SB-431542 is a Potent and Specific Inhibitor of Transforming Growth Factor-B Superfamily Type I Activin Receptor-like Kinase (ALK) Receptors ALK4, ALK5, and ALK7," Molecular Pharmacology 62-74: 65-74 (2002), which is hereby incorporated by reference in its entirety). SB431542 significantly attenuated radiation-induced α-SMA expression (FIGS. 13B-13C), confirming that radiation-driven activation of latent TGF-β plays a key role in radiation-induced myofibroblast differentiation.

Example 10

LDHA is Required for Radiation-Driven Myofibroblast Differentiation

Figure 14A:
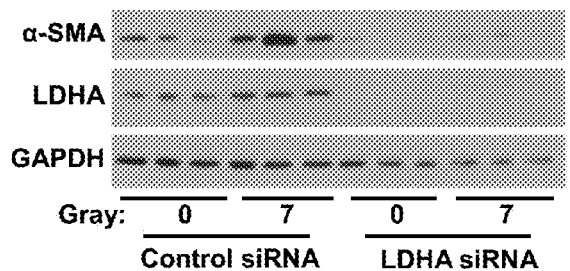
FIGS. 14A-D show that LDHA is required for radiation-driven myofibroblast differentiation. Primary human lung fibroblasts were transfected with either an LDHA siRNA pool or a non-targeting control siRNA pool 18 hours prior to exposure to 7 Gy irradiation.
Figure 14B:
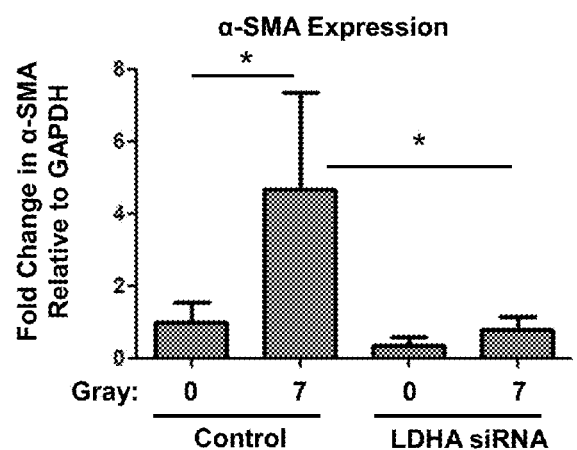
Figure 14C:
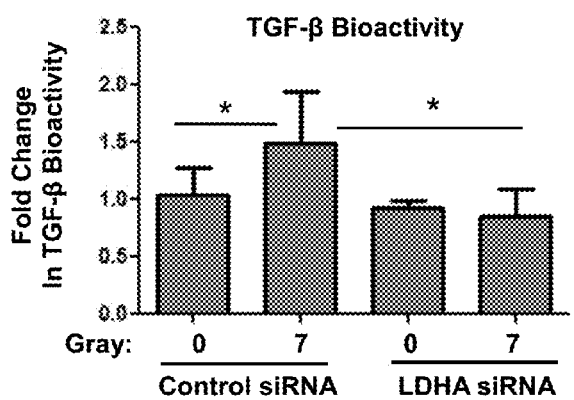
Figure 14D:
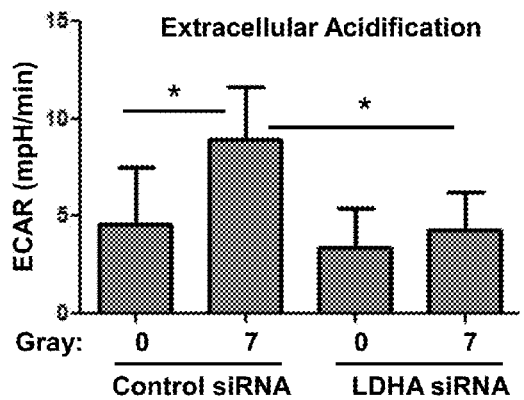

To determine whether increased lactate production is required for irradiation-driven myofibroblast differentiation, an siRNA approach was used to silence LDHA prior to irradiation. A high degree of LDHA knockdown was achieved (FIG. 14A). Ionizing radiation was unable to drive myofibroblast differentiation, as determined by α-SMA expression, in LDHA knockdown fibroblasts (FIGS. 14A-14B). LDHA siRNA also prevented radiation-induced TGF-β activation (FIG. 14C). Compared to control siRNA transfected cells, cells transfected with LDHA siRNA prior to radiation produced less lactate and had lower ECAR than cells transfected with control siRNA (FIG. 14D).

Example 11

Gossypol, an LDH Inhibitor, Inhibits Radiation-Induced Myofibroblast Differentiation It was next determined whether pharmacologic inhibition of LDHA would also prevent radiation induced myofibroblast differentiation. Pre-treatment of lung fibroblasts with gossypol prior to irradiation with 7 Gy strongly prevented radiation induced myofibroblast differentiation in a dose-dependent manner ($p \leq 0.001$) (FIGS. 15A-15B). Interestingly, gossypol also reduced baseline levels in α-SMA expression (FIGS. 15A-15B). Additionally, gossypol inhibited radiation-induced collagen production (FIG. 15C).

Discussion of Examples 6-11

The preceding Examples demonstrate for the first time that lactate plays a central role in radiation-induced pulmonary fibrosis. Ionizing radiation induces the expression of LDHA in lung fibroblasts, which leads to increased extracellular acidification, increased extracellular lactate, and increased TGF-β bioactivity (FIGS. 11-13). Expression of LDHA is required for efficient TGF-β bioactivity and fibroblast to myofibroblast differentiation, as siRNA knockdown of LDHA expression largely ablates the pro-fibrotic effect of irradiation (FIGS. 14A-14D). LDHA expression is also strongly upregulated in human and mouse lung radiation fibrosis tissue (FIGS. 10A-10C), supporting that this is a clinically important finding.

LDHA preferentially converts pyruvate to lactate and is up-regulated during hypoxia when oxygen is in limited supply for oxidative phosphorylation (Vander Heiden et al., "Understanding the Warburg Effect: The Metabolic Requirements of Cell Proliferation," Science 324:1029-1033 (2009), which is hereby incorporated by reference in its entirety). LDHA is also highly up-regulated in tumor cells regardless of oxygen tension, a phenomenon termed the Warburg effect (Hsu et al., "Cancer Cell Metabolism: Warburg and Beyond," Cell 134:703-707 (2008) and Vander Heiden et al., "Understanding the Warburg Effect: The Metabolic Requirements of Cell Proliferation," Science 324:1029-1033 (2009), which are hereby incorporated by reference in their entirety). The Warburg effect describes a highly glycolytic phenotype with a high production of lactate, regardless of whether oxygen is available for oxidative phosphorylation. Here, characteristics consistent with the Warburg effect in primary human lung fibroblasts exposed to radiation are reported, indicating that similar changes in metabolic pathways may be seen in radiation induced fibrosis and cancer.

Other metabolic similarities related to tumor growth are evident in pulmonary fibrosis, including uncontrolled cell proliferation and tissue invasion (Vancheri et al., "Idiopathic Pulmonary Fibrosis: A Disease with Similarities and Links to Cancer Biology," Eur. Resp. J. 35:496-504 (2010), which is hereby incorporated by reference in its entirety). Interestingly, consistent with highly metabolic tumors, patients with IPF have increased $^{18}$F-FDG metabolism in lung parenchyma when visualized with high resolution PET/CT, indicating that areas of fibrosis have increased glucose uptake (Groves et al., "Idiopathic Pulmonary Fibrosis and Diffuse Parenchymal Lung Disease: Implications from Initial Experience with 18F-FDG PET/CT," *J. Nuclear Med.* 50:538-545 (2009), which is hereby incorporated by reference in its entirety). Increased glucose uptake can contribute to accelerated growth and proliferation, a characteristic that is also consistent with fibroblasts from fibrotic lung tissue (Jordana et al., "Heterogeneous Proliferative Characteristics of Human Adult Lung Fibroblast Lines and Clonally Derived Fibroblasts from Control and Fibrotic Tissue," *Am. Rev. Respir. Dis.* 137:579-584 (1988) and Raghu et al., "Differential Proliferation of Fibroblasts Cultured From Normal and Fibrotic Human Lungs," *Am. Rev. Respir. Dis.* 138:703-708 (1988), which are hereby incorporated by reference in their entirety). Taken together with the results of increased LDHA expression in myofibroblasts in radiation-induced fibrosis (FIG. 10), it is believed that radiation causes changes in cellular metabolism in fibroblasts that are similar to changes seen in tumor cells to allow for increased proliferation to drive fibrosis.

It should be noted that while the direct effects of ionizing radiation on lung fibroblasts have been examined, it is possible that other lung cell types contribute to lactate production, extracellular acidification, and TGF-β activation in lung fibrosis. For example, some epithelial LDHA staining was observed in lung tissue from patients with radiation-induced pulmonary fibrosis (FIG. 10), as well as in IPF, sarcoidosis and nonspecific interstitial pneumonia (Kottmann et al., "Lactic Acid is Elevated in Idiopathic Pulmonary Fibrosis and Induces Myofibroblast Differentiation Via Ph-Dependent Activation of Transforming Growth Factor-Beta," *Am. J. Respir. Crit. Care Med.* 186:740-751 (2012), which is hereby incorporated by reference in its entirety). Epithelial cells may upregulate LDHA and lactate production, which then exerts a pro-fibrotic bystander effect on nearby fibroblasts. Other cellular sources of lactate during fibrogenesis will be investigated in future studies.

Examples 6-11 demonstrate that ionizing radiation leads to increased TGF-β bioactivity (FIG. 13) and that silencing LDHA with siRNA dampens this bioactivity and prevents radiation-induced extracellular acidification (FIG. 14). Applicants have previously shown that lactate activates TGF-β through a pH-dependent mechanism (Kottmann et al., "Lactic Acid is Elevated in Idiopathic Pulmonary Fibrosis and Induces Myofibroblast Differentiation Via Ph-Dependent Activation of Transforming Growth Factor-Beta," *Am. J. Respir. Crit. Care Med.* 186:740-751 (2012), which is hereby incorporated by reference in its entirety). It is well-established that radiation causes induction of TGF-β (Barcellos-Hoff et al., "Transforming Growth Factor-Beta Activation in Irradiated Murine Mammary Gland," *J. Clin. Invest.* 93:892-899 (1994), Martin et al., "TGF-β1 and Radiation Fibrosis: A Master Switch and the Specific Therapeutic Target?" *Int. J. Rad. Oncol. Biol. Phys.* 47:277-290 (2000), and Yi et al., "Radiation-Induced Lung Injury In Vivo: Expression of Transforming Growth Factor-Beta Precedes Fibrosis," *Inflammation* 20:339-352 (1996), which are hereby incorporated by reference in their entirety), though the mechanisms of radiation-induced TGF-β activation are poorly understood. One proposed mechanism is oxidation dependent activation through redox related mechanisms (Barcellos-Hoff et al., "Redox-Mediated Activation of Latent Transforming Growth Factor-Beta 1," *Mol. Endocrinol.* 10:1077-1083 (1996), which is hereby incorporated by reference in its entirety). Activation through redox mechanisms would likely occur very quickly following radiation, given that reactive oxygen species induced by ionizing radiation are short lived (Leach et al., "Ionizing Radiation-Induced, Mitochondria-Dependent Generation of Reactive Oxygen/Nitrogen," *Cancer Res.* 61:3894-3901 (2001), which is hereby incorporated by reference in its entirety). Based on the results presented in the preceding Examples, it is believed that radiation also causes TGF-β activation via extracellular acidification from increased lactate production, which would provide a mechanism for long-term and sustained TGF-β bioactivity during fibrosis. Given that TGF-β can induce expression of LDHA (Kottmann et al., "Lactic Acid is Elevated in Idiopathic Pulmonary Fibrosis and Induces Myofibroblast Differentiation Via pH-Dependent Activation of Transforming Growth Factor-Beta," *Am. J. Respir. Crit. Care Med.* 186:740-751 (2012), which is hereby incorporated by reference in its entirety), a positive feed-forward loop in which radiation causes extracellular acidification that activate latent TGF-β, which can further induce LDHA, is proposed. Therefore, it is useful to interrupt this fibrotic feed-forward loop when designing therapies for radiation-induced pulmonary fibrosis.

Inhibition of LDHA is an area of active research in the oncology field since LDHA overexpression is associated with cancer cell growth, poor prognosis and drug resistance (Augoff et al., "Lactate Dehydrogenase 5: An Old Friend and a New Hope in the War on Cancer," *Cancer Lett.* 358(1): 1-7(2015); Fantin et al., "Attenuation of LDH-A Expression Uncovers a Link Between Glycolysis, Mitochondrial Physiology, and Tumor Maintenance," *Cancer Cell* 9:425-434 (2006); Xie et al., "Targeting Lactate Dehydrogenase-A Inhibits Tumorigenesis and Tumor Progression in Mouse Models of Lung Cancer and Impacts Tumor-Initiating Cells," *Cell Metabolism* 19:795-809 (2014); and Zhao et al., "Targeting Cellular Metabolism to Improve Cancer Therapeutics," *Cell Death Dis.* 4:e532 (2013), which are hereby incorporated by reference in their entirety). Here, genetic knockdown of LDHA expression prevented radiation-induced myofibroblast differentiation (FIG. 14). However, therapeutic gene silencing in patients presents several technical hurdles. Gossypol, a potent LDHA inhibitor derived from cottonseed (Granchi et al., "Inhibitors of Lactate Dehydrogenase Isoforms and their Therapeutic Potentials," *Curr. Med. Chem.* 17:672-697 (2010) and Lee et al., "Enzyme Inactivation and Inhibition by Gossypol," *Mol. Cell Biochem.* 47:65-70 (1982), which are hereby incorporated by reference in their entirety) has been explored as a novel pharmaceutical therapy in breast cancer (Van Poznak et al., "Oral Gossypol in the Treatment of Patients with Refractory Metastatic Breast Cancer: A Phase I/II Clinical Trial," *Breast Cancer Res. Treatment* 66:239-248 (2001), which is hereby incorporated by reference in its entirety), and has been shown to have anti-tumorigenic effects in breast and colon cancer cells (Gilbert et al., "Antiproliferative Activity of Gossypol and Gossypolone on Human Breast Cancer Cells," *Life Sci.* 57:61-67 (1995); Tuszynski et al., "Differential Cytotoxic Effect of Gossypol on Human Melanoma, Colon Carcinoma, and Other Tissue Culture Cell Lines," *Cancer Res.* 44:768-771 (1984); and Van Poznak et al., "Oral Gossypol in the Treatment of Patients with Refractory Metastatic Breast Cancer: A Phase I/II Clinical Trial," *Breast Cancer Res. Treatment* 66:239-248 (2001), which are hereby incorporated by reference in their entirety). These results show that gossypol potently inhibits myofibroblast differentiation, with similar efficacy to genetic knockdown.

It should be noted that gossypol may have other effects in addition to LDH inhibition including induction of apoptosis, modulation of cell cycle regulatory proteins and/or inhibition of other enzymatic activities (Oliver et al., "(−)-Gossypol Acts Directly on the Mitochondria to Overcome Bcl-2- and Bcl-XL-Mediated Apoptosis Resistance," *Mol. Cancer Therapeutics* 4:23-31 (2005), which is hereby incorporated by reference in its entierty). These so-called off-target effects may in fact be beneficial in the context of fibrosis. For example, resistance to apoptosis by myofibroblasts is believed to contribute to the pathogenesis of fibrosis in vivo (Horowitz et al., "Activation of the Pro-Survival Phosphatidylinositol 3-Kinase/AKT Pathway by Transforming Growth Factor-Beta1 in Mesenchymal Cells is Mediated by p38 MAPK-Dependent Induction of an Autocrine Growth Factor," *J. Biol. Chem.* 279:1359-1367 (2004) and Yoshida et al., "MAP Kinase Activation and Apoptosis in Lung Tissues from Patients with Idiopathic Pulmonary Fibrosis," *J. Pathol.* 198:388-396 (2002), which is hereby incorporated by reference in its entirety). These results are the first proof of principle that inhibition of LDHA activity may have therapeutic benefit in lung fibrosis.

Prospective

Example 12

In Vivo Administration of Gossypol to Treat Radiation-Induced Pulmonary Fibrosis To examine the effects of gossypol on radiation-induced pulmonary fibrosis at 26 weeks, groups of C57BL/6 mice (10 per group) will be exposed to 5 Gray TBI plus 10 Gray thoracic radiation, and subcutaneous gossypol treatment will be initiated at week two at 1, 5 and 10 mg/kg/day. Gossypol treatment will be continued through week 26. Control groups will include non-irradiated mice treated with vehicle alone, irradiated mice treated with vehicle alone and mice treated with Gossypol alone (highest dose). Blood draws will be performed at 4, 8 and 26 weeks post irradiation and plasma levels of club cell secretory protein (CCSP), a sensitive indicator of epithelial damage, will be measured. Following euthanasia at 26 weeks, lung fibrosis will be evaluated by established protocols including histological scoring of tissue sections and determination of markers of myofibroblast differentiation (LDH, αSMA and calponin) and ECM proteins (hydroxyproline, collagen I, collagen III, and fibronectin) by Western blot and qPCR analysis. Lactate levels and LDH activity will be assessed in tissue homogenates, and active TGF-β will be determined using the mink lung cell bioassay. Mice will be treated in groups of 10, which was previously determined to afford 80% statistical power to demonstrate a reduction in fibrosis of 25% or greater. Statistical significance will be assessed by ANOVA with post-hoc correction.

Prospective

Example 13

In Vivo Administration of Additional LDH Inhibitors to Treat Radiation-Induced Pulmonary Fibrosis Example 12 will be repeated using alternative LDH inhibitors, including one or more compounds of formula (I, Ia, or Ib), the gossypol derivative FX11, and/or elesclomol, at 1, 5 and 10 mg/kg/day, and their efficacy will be assessed using the same protocols.

Having thus described the basic concept of the technology, it will be rather apparent to those skilled in the art that the foregoing detailed disclosure is intended to be presented by way of example only, and is not limiting. It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of treating a fibrotic condition in an individual, said method comprising:
administering to an individual having a fibrotic condition an effect amount of a lactic dehydrogenase (LDH) inhibitor, wherein the fibrotic condition involves an internal organ or tissue, or ocular tissue, and said administering is effective to treat the fibrotic condition, and wherein the fibrotic condition is not a cancerous proliferative disorder, idiopathic arthrofibrosis, or dermatological scarring.

2. The method according to claim 1, wherein the method consists of said administering.

3. The method according to claim 1, wherein the method excludes administration of a cancer therapy.

4. The method according to claim 1, wherein the LDH inhibitor is an LDH5 inhibitor.

5. The method according to claim 1, wherein the LDH inhibitor is an RNAi specific for LDH, oxamate, gossypol, galloflavin, 3-hydroxyisoxazole-4-carboxylic acid (HICA), 4-hydroxy-1,2,5-thiadiazole-3-carboxylic acid (HTCA), a derivative of 8-deoxyhemigossylic (2,3-dihydroxynaphtalen-1-carboxylic) acid, an N-hydroxyindole-based inhibitor designated FX11, or elesclomol.

6. The method according to claim 1, wherein the LDH inhibitor is a compound according to formula (I):

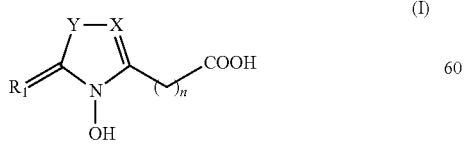

(I)

wherein:
n is selected from the group consisting of: 0 and 1;
X is selected from the group consisting of: N, $N^+$—$O^-$, and C—Z;
Y is selected from the group consisting of: S, O, and C=$R^2$;
Z is selected from the group consisting of: hydrogen, $OR^A$, $NR^AR^B$, halogen, cyano, nitro, alkoxy, aryloxy, heteroaryloxy, —C(O)$C_{1-6}$-alkyl, —C(O)phenyl, —C(O)benzyl, —C(O)$C_{5-6}$-heterocycle, —S—$C_{1-6}$-alkyl, —S-phenyl, —S-benzyl, —S—$C_{5-6}$-heterocycle, —S(O)$C_{1-6}$-alkyl, —S(O)phenyl, —S(O)benzyl—S(O)$_2C_{5-6}$-heterocycle, —S(O)$_2C_{1-6}$-alkyl, —S(O)$_2$phenyl, —S(O)$_2$benzyl, —S(O)$_2C_{5-6}$-heterocycle, —S(O)$_2$$NR^AR^B$, $C_{1-6}$-alkyl, halo-$C_{1-6}$-alkyl, dihalo-$C_{1-6}$-alkyl, trihalo-$C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, phenyl, benzyl, and $C_{5-6}$-heterocycle;
$R^1$ is selected from:

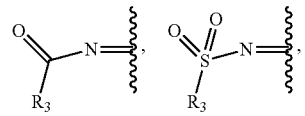

and $R^2$ together with $R^1$ is

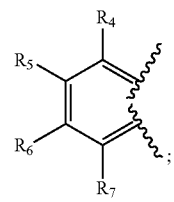

$R^3$ is selected from the group consisting of: hydrogen, $C_{1-4}$-alkyl, halo-$C_{1-4}$-alkyl, dihalo-$C_{1-4}$-alkyl, trihalo-$C_{1-4}$-alkyl, $C_{2-6}$-alkenyl, $C_{2-4}$-alkynyl, $C_{3-6}$-cycloalkyl, $C_{3-6}$-cycloalkyl-$C_{1-2}$-alkyl, phenyl, benzyl, and $C_{5-6}$-heterocycle;

R$^4$, R$^5$, R$^6$, R$^7$ are independently selected from the group consisting of: hydrogen, OR$^A$, NR$^A$R$^B$, —C(O)R$^A$, —C(O)OR$^A$, —C(O)NR$^A$R$^B$, halogen, cyano, nitro, alkoxy, aryloxy, heteroaryloxy, —C(O)C$_{1-6}$-alkyl, —C(O)phenyl, —C(O)benzyl, —C(O)C$_{5-6}$-heterocycle, —S—C$_{1-6}$-alkyl, —S-phenyl, —S-benzyl, —S—C$_{5-6}$-heterocycle, —S(O)C$_{1-6}$-alkyl, —S(O)phenyl, —S(O)benzyl, —S(O)C$_{5-6}$-heterocycle, —S(O)$_2$C$_{1-6}$-alkyl, —S(O)$_2$phenyl, —S(O)$_2$benzyl, —S(O)$_2$C$_{5-6}$-heterocycle, —S(O)$_2$NR$^A$R$^B$, C$_{1-6}$-alkyl, halo-C$_{1-6}$-alkyl, dihalo-C$_{1-6}$-alkyl, trihalo-C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, phenyl, benzyl, naphthyl, and C$_{5-6}$-heterocycle;

wherein the phenyl, benzyl, naphthyl and C$_{5-6}$ heterocycle of the R$^3$, R$^4$R$^5$, R$^6$, R$^7$, R$^A$, or R$^B$ group may optionally be substituted with 1 to 3 groups independently selected from OR$^C$ wherein two OR$^C$ groups may concur into forming a cycle, NR$^C$R$^D$, —C(O)R$^C$, —C(O)OR$^C$, C$_{1-4}$-alkyl-OR$^C$, C$_{1-4}$-alkyl-C(O)OR$^C$, —C(O)NR$^C$R$^D$, —S(O)$_{2NR}$$^C$R$^D$, —S(O)$_2$C$_{1-6}$-alkyl, halogen, cyano, nitro, C$_{1-4}$-alkyl, halo-C$_{1-4}$-alkyl, dihalo-C$_{1-4}$-alkyl, trihalo-C$_{1-4}$-alkyl, aryl or heteroaryl optionally substituted with C(O)OR$^C$;

wherein any atom of the C$_5$-C$_6$ heterocycle of the R$^3$, R$^4$, R$^5$, R$^6$ and R$^7$ group may be bound to an oxygen so as to form an oxo or a sulfoxo moiety;

wherein any alkyl, alkenyl and alkynyl groups of the R$^A$, R$^B$, R$^4$, R$^5$, R$^6$ or R$^7$ may optionally be substituted with 1-3 groups independently selected from OR$^C$, NR$^C$R$^D$, halogen, cyano and nitro;

wherein any carbon-bound hydrogen atom may be substituted with a fluorine atom; and R$^A$, R$^B$, R$^C$ and R$^D$ are independently selected from the group consisting of: hydrogen, —C(O)C$_{1-6}$-alkyl, —C(O)phenyl, —C(O)benzyl, —C(O)C$_{5-6}$-heterocycle, —S(O)$_2$C$_{1-6}$alkyl, —S(O)$_2$phenyl, —S(O)$_2$benzyl, —S(O)$_2$C$_{5-6}$-heterocycle, C$_{1-6}$-alkyl, halo-C$_{1-6}$-alkyl, dihalo-C$_{1-6}$-alkyl, trihalo-C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, phenyl, benzyl, and C$_{5-6}$-heterocycle.

7. The method of claim 1, wherein said internal organ comprises lung, liver, kidney, heart, pancreas, gastrointestinal organs, or genitourinary organs.

8. The method of claim 1, wherein said internal tissue comprises vascular tissue.

9. The method of claim 1, wherein said ocular tissue comprises corneal tissue or retinal tissue.

10. The method of claim 1, wherein the fibrosis is pulmonary fibrosis.

11. The method of claim 1, wherein said administering is effective to inhibit one or more of TGF-β-induced myofibroblast differentiation, pro-fibrotic gene expression, lactic acid production that reduces extracellular pH, and progression of the fibrosis.

12. The method of claim 1, wherein said administering is carried out orally, parenterally, periadventitially, subcutaneously, intravenously, intramuscularly, intraperitoneally, by inhalation, by intranasal instillation, by implantation, by intracavitary or intravesical instillation, intraocularly, intraarterially, intralesionally, transdermally, intradermally or by application to mucous membranes.

13. The method according to claim 1, further comprising administering at least one additional anti-fibrotic agent to the individual.

14. The method according to claim 13, wherein said additional anti-fibrotic agent is selected from the group consisting of calcium channel blockers, cytotoxic agents, cytokines, chemokines, integrins, growth factors, hormones, lysophosphatidic acid (LPA) receptor 1 antagonists, agents that modulate the TGF-β pathway, endothelin receptor antagonists, agents that reduce connective tissue growth factor (CTGF) activity, matrix metalloproteinase (MMP) inhibitors, agents that reduce the activity of platelet-derived growth factor (PDGF), agents that interfere with integrin function, agents that interfere with the pro-fibrotic activities of cytokines, agents that reduce oxidative stress, PDE4 inhibitors, PDE5 inhibitors, mTor inhibitors, modifiers of the arachidonic acid pathway, peroxisome proliferator-activated receptor (PPAR)-γ agonists, kinase inhibitors, inhibitors of VEGF signaling pathway, matrix metalloproteinases, tissue inhibitors of metalloproteinases (TIMPs), HGF agonists, angiotensin-converting enzyme (ACE) inhibitors, angiotensin receptor antagonists, inhibitors of advanced glycation endproducts (AGEs) or their receptors (RAGEs), Rho kinase inhibitors, PKC inhibitors, ADAM-10 inhibitor, farnesoid X receptor agonists, caspase inhibitors, anti-oxidants, inhibitors of collagen expression, LMW heparin or heparin analogs, copper chelators, TNF-α blocking agents, HMG-CoA reductase inhibitors, and Thy-1 (CD90) inhibitors.

15. The method according to claim 13, wherein said administering of the at least one additional anti-fibrotic agent is carried out orally, parenterally, periadventitially, subcutaneously, intravenously, intramuscularly, intraperitoneally, by inhalation, by intranasal instillation, by implantation, by intracavitary or intravesical instillation, intraocularly, intraarterially, intralesionally, transdermally, intradermally or by application to mucous membranes.

* * * * *

UNITED STATES PATENT AND TRADEMARK OFFICE
CERTIFICATE OF CORRECTION

PATENT NO. : 9,750,761 B2
APPLICATION NO. : 14/718933
DATED : September 5, 2017
INVENTOR(S) : Kottmann et al.

It is certified that error appears in the above-identified patent and that said Letters Patent is hereby corrected as shown below:

In the Claims

In Claim 1, at Column 43, Line 36, delete "effect" and insert -- effective --.

In Claim 6, at Column 45, Line 16, insert -- , -- between "$R^4$" and "$R^5$".

In Claim 6, at Column 45, Line 21, delete "$-S(O)_{2NR}{}^{C}R^{D}$" and insert -- $-S(O)_2NR^{C}R^{D}$ --.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 12

<210> SEQ ID NO 1
<211> LENGTH: 19
<212> TYPE: DNA
<213> ORGANISM: Artificial
<220> FEATURE:
<223> OTHER INFORMATION: LDHa siRNA target sequence

<400> SEQUENCE: 1
ctcgattccg ttatctgat        19

<210> SEQ ID NO 2
<211> LENGTH: 29
<212> TYPE: DNA
<213> ORGANISM: Artificial
<220> FEATURE:
<223> OTHER INFORMATION: LDHa shRNA target sequence

<400> SEQUENCE: 2
gccgagagca taatgaagaa ccttaggcg        29

<210> SEQ ID NO 3
<211> LENGTH: 20
<212> TYPE: DNA
<213> ORGANISM: Artificial

-continued

```
<220> FEATURE:
<223> OTHER INFORMATION: Forward primer for human 18S

<400> SEQUENCE: 3
ggtcgctcgc tcctctccca                                          20

<210> SEQ ID NO 4
<211> LENGTH: 20
<212> TYPE: DNA
<213> ORGANISM: Artificial
<220> FEATURE:
<223> OTHER INFORMATION: Reverse primer for human 18S

<400> SEQUENCE: 4
aggggctgac cgggttggtt                                          20

<210> SEQ ID NO 5
<211> LENGTH: 22
<212> TYPE: DNA
<213> ORGANISM: Artificial
<220> FEATURE:
<223> OTHER INFORMATION: Forward primer for human Col1a1

<400> SEQUENCE: 5
ttgaaggagg atgttcccat ct                                       22

<210> SEQ ID NO 6
<211> LENGTH: 23
<212> TYPE: DNA
<213> ORGANISM: Artificial
<220> FEATURE:
<223> OTHER INFORMATION: Reverse primer for human Col1a1

<400> SEQUENCE: 6
acagacacat atttggcatg gtt                                      23

<210> SEQ ID NO 7
<211> LENGTH: 22
<212> TYPE: DNA
<213> ORGANISM: Artificial
<220> FEATURE:
<223> OTHER INFORMATION: Forward primer for human Col3a1

<400> SEQUENCE: 7
ttgaaggagg atgttcccat ct                                       22

<210> SEQ ID NO 8
<211> LENGTH: 23
<212> TYPE: DNA
<213> ORGANISM: Artificial
<220> FEATURE:
<223> OTHER INFORMATION: Reverse primer for human Col3a1

<400> SEQUENCE: 8
acagacacat atttggcatg gtt                                      23

<210> SEQ ID NO 9
<211> LENGTH: 22
<212> TYPE: DNA
<213> ORGANISM: Artificial
<220> FEATURE:
<223> OTHER INFORMATION: Forward primer for mouse 18S

<400> SEQUENCE: 9
gcttgctcgc gcttccttac ct                                       22
```

```
<210> SEQ ID NO 10
<211> LENGTH: 21
<212> TYPE: DNA
<213> ORGANISM: Artificial
<220> FEATURE:
<223> OTHER INFORMATION: Reverse primer for mouse 18S

<400> SEQUENCE: 10
tcactgtacc ggccgtgcgt a                                          21

<210> SEQ ID NO 11
<211> LENGTH: 20
<212> TYPE: DNA
<213> ORGANISM: Artificial
<220> FEATURE:
<223> OTHER INFORMATION: Forward primer for mouse LDHA

<400> SEQUENCE: 11
tggcgactcc agtgtgcctg                                            20

<210> SEQ ID NO 12
<211> LENGTH: 21
<212> TYPE: DNA
<213> ORGANISM: Artificial
<220> FEATURE:
<223> OTHER INFORMATION: Reverse primer for mouse LDHA

<400> SEQUENCE: 12
aggcactgtc caccacctgc t                                          21
```